US010309614B1

(12) United States Patent
Jones et al.

(10) Patent No.: US 10,309,614 B1
(45) Date of Patent: Jun. 4, 2019

(54) LIGHT DIRECTING ELEMENT

(71) Applicant: Vital Vio, Inc., Troy, NY (US)

(72) Inventors: Nicholas Jones, Mechanicville, NY (US); Aram Kuzmak, Troy, NY (US); Cori Winslow, Ballston Spa, NY (US); Robert Barron, Port Washington, NY (US)

(73) Assignee: Vital Vivo, Inc., Troy, NY (US)

( * ) Notice: Subject to any disclaimer, the term of this patent is extended or adjusted under 35 U.S.C. 154(b) by 0 days.

(21) Appl. No.: 16/022,440

(22) Filed: Jun. 28, 2018

Related U.S. Application Data

(60) Provisional application No. 62/594,802, filed on Dec. 5, 2017.

(51) Int. Cl.
*F21V 7/00* (2006.01)
*F21V 13/04* (2006.01)
*A61L 2/10* (2006.01)
*F21V 7/04* (2006.01)

(52) U.S. Cl.
CPC .............. *F21V 7/0025* (2013.01); *A61L 2/10* (2013.01); *F21V 7/041* (2013.01); *F21V 13/04* (2013.01)

(58) Field of Classification Search
CPC ........ F21V 7/0025; F21V 7/041; F21V 13/04; A61L 2/10
See application file for complete search history.

(56) References Cited

U.S. PATENT DOCUMENTS

| 1,493,820 | A | 5/1924 | Miller et al. |
| 2,622,409 | A | 12/1952 | Stimkorb |
| 2,773,715 | A | 12/1956 | Lindner |
| 3,314,746 | A | 4/1967 | Millar |
| 3,670,193 | A | 6/1972 | Thorington et al. |
| 3,791,864 | A | 2/1974 | Steingroever |
| 3,926,556 | A | 12/1975 | Boucher |

(Continued)

FOREIGN PATENT DOCUMENTS

| CN | 201396611 Y | 2/2010 |
| CN | 102213382 A | 10/2011 |

(Continued)

OTHER PUBLICATIONS

Jappe, U., "Pathological mechanisms of acne with special emphasis on Propionibacterium acnes and related therapy," Acta Dermato-Venereologica, 2003, vol. 83, pp. 241-248.

(Continued)

*Primary Examiner* — Anh T Mai
*Assistant Examiner* — Glenn D Zimmerman
(74) *Attorney, Agent, or Firm* — Banner & Witcoff, Ltd.

(57) ABSTRACT

Light directing elements, methods, and systems are disclosed. An example light directing element may comprise an elongated body having a first end, a second end and an exterior surface, the elongated body being transparent or translucent to permit transmission of light axially and radially therethrough, a light emitter disposed at the first end of the elongated body, and a diffuser including at least one reflective element disposed within the elongated body, wherein the diffuser is configured to redirect axially emitted light from the light emitter radially towards the exterior surface and wherein the diffuser expands in cross-section towards the second end.

17 Claims, 13 Drawing Sheets

(56) References Cited

U.S. PATENT DOCUMENTS

| | | | |
|---|---|---|---|
| 3,992,646 | A | 11/1976 | Corth |
| 4,121,107 | A | 10/1978 | Bachmann |
| 4,461,977 | A | 7/1984 | Pierpoint et al. |
| 4,576,436 | A | 3/1986 | Daniel |
| 4,867,052 | A | 9/1989 | Cipelletti |
| 4,892,712 | A | 1/1990 | Robertson et al. |
| 4,910,942 | A | 3/1990 | Dunn et al. |
| 5,231,472 | A | 7/1993 | Marcus et al. |
| 5,489,827 | A | 2/1996 | Xia |
| 5,530,322 | A | 6/1996 | Ference et al. |
| 5,559,681 | A | 9/1996 | Duarte |
| 5,668,446 | A | 9/1997 | Baker |
| 5,721,471 | A | 2/1998 | Begemann et al. |
| 5,725,148 | A | 3/1998 | Hartman |
| 5,800,479 | A | 9/1998 | Thiberg |
| 5,901,564 | A | 5/1999 | Comeau, II |
| 5,962,989 | A | 10/1999 | Baker |
| 6,031,958 | A * | 2/2000 | McGaffigan ..... B29D 11/00663 362/555 |
| 6,166,496 | A | 12/2000 | Lys et al. |
| 6,183,500 | B1 | 2/2001 | Kohler |
| 6,242,752 | B1 | 6/2001 | Soma et al. |
| 6,246,169 | B1 | 6/2001 | Pruvot |
| 6,251,127 | B1 | 6/2001 | Biel |
| 6,379,022 | B1 | 4/2002 | Amerson et al. |
| 6,477,853 | B1 | 11/2002 | Khorram |
| 6,524,529 | B1 | 2/2003 | Horton, III |
| 6,551,346 | B2 | 4/2003 | Crossley |
| 6,554,439 | B1 | 4/2003 | Teicher et al. |
| 6,627,730 | B1 | 9/2003 | Bumie |
| 6,676,655 | B2 | 1/2004 | McDaniel |
| 6,791,259 | B1 | 9/2004 | Stokes et al. |
| 6,902,807 | B1 | 6/2005 | Argoitia et al. |
| 7,015,636 | B2 | 3/2006 | Bolta |
| 7,175,807 | B1 | 2/2007 | Jones |
| 7,190,126 | B1 | 3/2007 | Paton |
| 7,198,634 | B2 | 4/2007 | Harth et al. |
| 7,201,767 | B2 | 4/2007 | Bhullar |
| 7,213,941 | B2 | 5/2007 | Sloan et al. |
| 7,438,719 | B2 | 10/2008 | Chung et al. |
| 7,503,675 | B2 | 3/2009 | Demarest et al. |
| 7,516,572 | B2 | 4/2009 | Yang et al. |
| 7,521,875 | B2 | 4/2009 | Maxik |
| 7,611,156 | B2 | 11/2009 | Dunser |
| 7,612,492 | B2 | 11/2009 | Lestician |
| 7,658,891 | B1 | 2/2010 | Barnes |
| 7,955,695 | B2 | 6/2011 | Argoitia |
| 8,035,320 | B2 | 10/2011 | Sibert |
| 8,214,084 | B2 | 7/2012 | Ivey et al. |
| 8,232,745 | B2 | 7/2012 | Chemel et al. |
| 8,357,914 | B1 | 1/2013 | Caldwell |
| 8,398,264 | B2 | 3/2013 | Anderson et al. |
| 8,476,844 | B2 | 7/2013 | Hancock et al. |
| 8,481,970 | B2 | 7/2013 | Cooper et al. |
| 8,506,612 | B2 | 8/2013 | Ashdown |
| 8,508,204 | B2 | 8/2013 | Deurenberg et al. |
| 8,761,565 | B1 | 6/2014 | Coleman et al. |
| 8,886,361 | B1 | 11/2014 | Harmon et al. |
| 8,895,940 | B2 | 11/2014 | Moskowitz et al. |
| 8,999,237 | B2 | 4/2015 | Tumanov |
| 9,024,276 | B2 | 5/2015 | Pugh et al. |
| 9,027,479 | B2 | 5/2015 | Raksha et al. |
| 9,028,084 | B2 | 5/2015 | Maeng et al. |
| 9,039,966 | B2 | 5/2015 | Anderson et al. |
| 9,046,227 | B2 | 6/2015 | David et al. |
| 9,078,306 | B2 | 7/2015 | Mans et al. |
| 9,119,240 | B2 | 8/2015 | Nagazoe |
| 9,173,276 | B2 | 10/2015 | Van Der Veen et al. |
| 9,257,059 | B2 | 2/2016 | Raksha et al. |
| 9,283,292 | B2 | 3/2016 | Kretschmann |
| 9,313,860 | B2 | 4/2016 | Wingren |
| 9,323,894 | B2 | 4/2016 | Kiani |
| 9,333,274 | B2 | 5/2016 | Peterson et al. |
| 9,368,695 | B2 | 6/2016 | David et al. |
| 9,410,664 | B2 | 8/2016 | Krames et al. |
| 9,420,671 | B1 | 8/2016 | Sugimoto et al. |
| 9,433,051 | B2 | 8/2016 | Snijder et al. |
| 9,439,271 | B2 | 9/2016 | Ku et al. |
| 9,439,989 | B2 | 9/2016 | Lalicki et al. |
| 9,492,576 | B1 | 11/2016 | Cudak et al. |
| 9,581,310 | B2 | 2/2017 | Wu et al. |
| 9,623,138 | B2 | 4/2017 | Pagan et al. |
| 9,625,137 | B2 | 4/2017 | Li et al. |
| 9,681,510 | B2 | 6/2017 | van de Ven |
| 2002/0074559 | A1 | 6/2002 | Dowling et al. |
| 2002/0122743 | A1 | 9/2002 | Huang |
| 2003/0009158 | A1 | 1/2003 | Perricone |
| 2003/0019222 | A1 | 1/2003 | Takahashi et al. |
| 2003/0023284 | A1 | 1/2003 | Gartstein et al. |
| 2003/0124023 | A1 | 7/2003 | Burgess et al. |
| 2003/0178632 | A1 | 9/2003 | Hohn et al. |
| 2003/0231485 | A1 | 12/2003 | Chien |
| 2004/0008523 | A1 | 1/2004 | Butler |
| 2004/0010299 | A1 | 1/2004 | Tolkoff et al. |
| 2004/0024431 | A1 | 2/2004 | Carlet |
| 2004/0039242 | A1 | 2/2004 | Tolkoff et al. |
| 2004/0047142 | A1 | 3/2004 | Goslee |
| 2004/0147986 | A1 | 7/2004 | Baumgardner et al. |
| 2004/0158541 | A1 | 8/2004 | Notarianni et al. |
| 2004/0159039 | A1 | 8/2004 | Yates et al. |
| 2004/0230259 | A1 | 11/2004 | Di Matteo |
| 2004/0262595 | A1 | 12/2004 | Mears et al. |
| 2004/0266546 | A1 | 12/2004 | Huang |
| 2005/0055070 | A1 | 3/2005 | Jones et al. |
| 2005/0104059 | A1 | 5/2005 | Friedman et al. |
| 2005/0107849 | A1 | 5/2005 | Altshuler et al. |
| 2005/0107853 | A1 | 5/2005 | Krespi et al. |
| 2005/0159795 | A1 | 7/2005 | Savage et al. |
| 2005/0207159 | A1 | 9/2005 | Maxik |
| 2005/0267233 | A1 | 12/2005 | Joshi |
| 2006/0006678 | A1 | 1/2006 | Herron |
| 2006/0009822 | A1 | 1/2006 | Savage et al. |
| 2006/0022582 | A1 | 2/2006 | Radkov |
| 2006/0071589 | A1 | 4/2006 | Radkov |
| 2006/0085052 | A1 | 4/2006 | Feuerstein et al. |
| 2006/0138435 | A1 | 6/2006 | Tarsa et al. |
| 2006/0186377 | A1 | 8/2006 | Takahashi et al. |
| 2006/0230576 | A1 | 10/2006 | Meine |
| 2006/0247741 | A1 | 11/2006 | Hsu et al. |
| 2006/0262545 | A1 | 11/2006 | Piepgras et al. |
| 2007/0023710 | A1 | 2/2007 | Tom et al. |
| 2007/0061050 | A1 | 3/2007 | Hoffknecht |
| 2007/0115665 | A1 | 5/2007 | Mueller et al. |
| 2007/0164232 | A1 | 7/2007 | Rolleri et al. |
| 2007/0258851 | A1 | 11/2007 | Fogg et al. |
| 2008/0008620 | A1 | 1/2008 | Alexiadis |
| 2008/0015560 | A1 * | 1/2008 | Gowda ................. A61N 5/062 606/15 |
| 2008/0091250 | A1 | 4/2008 | Powell |
| 2008/0278927 | A1 | 11/2008 | Li et al. |
| 2008/0305004 | A1 | 12/2008 | Anderson et al. |
| 2009/0018621 | A1 | 1/2009 | Vogler et al. |
| 2009/0034236 | A1 | 2/2009 | Reuben |
| 2009/0076115 | A1 | 3/2009 | Wharton et al. |
| 2009/0154167 | A1 | 6/2009 | Lin |
| 2009/0231832 | A1 | 9/2009 | Zukauskas et al. |
| 2009/0285727 | A1 | 11/2009 | Levy |
| 2010/0001648 | A1 | 1/2010 | De Clercq et al. |
| 2010/0027259 | A1 | 2/2010 | Simon et al. |
| 2010/0071257 | A1 | 3/2010 | Tsai |
| 2010/0090935 | A1 | 4/2010 | Tseng et al. |
| 2010/0107991 | A1 | 5/2010 | Elrod et al. |
| 2010/0121420 | A1 | 5/2010 | Fiset et al. |
| 2010/0148083 | A1 | 6/2010 | Brown et al. |
| 2010/0179469 | A1 | 7/2010 | Hammond et al. |
| 2010/0232135 | A1 | 9/2010 | Munehiro et al. |
| 2010/0246169 | A1 | 9/2010 | Anderson et al. |
| 2011/0063835 | A1 | 3/2011 | Rivas et al. |
| 2011/0084614 | A1 | 4/2011 | Eisele et al. |
| 2011/0256019 | A1 | 10/2011 | Gruen et al. |
| 2012/0025717 | A1 | 2/2012 | Klusmann et al. |
| 2012/0043552 | A1 | 2/2012 | David et al. |
| 2012/0161170 | A1 | 6/2012 | Dubuc et al. |
| 2012/0280147 | A1 | 11/2012 | Douglas |

(56) References Cited

U.S. PATENT DOCUMENTS

| | | |
|---|---|---|
| 2012/0281408 A1 | 11/2012 | Owen et al. |
| 2012/0315626 A1 | 12/2012 | Nishikawa et al. |
| 2012/0320607 A1 | 12/2012 | Kinomoto et al. |
| 2013/0010460 A1 | 1/2013 | Peil et al. |
| 2013/0045132 A1 | 2/2013 | Tumanov |
| 2013/0077299 A1 | 3/2013 | Russell et al. |
| 2013/0200279 A1 | 8/2013 | Chuang |
| 2013/0298445 A1 | 11/2013 | Aoki et al. |
| 2013/0313516 A1 | 11/2013 | David et al. |
| 2013/0313546 A1 | 11/2013 | Yu |
| 2014/0061509 A1 | 3/2014 | Shur et al. |
| 2014/0209944 A1 | 7/2014 | Kim et al. |
| 2014/0225137 A1 | 8/2014 | Krames et al. |
| 2014/0254131 A1 | 9/2014 | Osinski et al. |
| 2014/0301062 A1 | 10/2014 | David et al. |
| 2014/0328046 A1 | 11/2014 | Aanegola et al. |
| 2015/0062892 A1 | 3/2015 | Krames et al. |
| 2015/0068292 A1 | 3/2015 | Su et al. |
| 2015/0086420 A1 | 3/2015 | Trapani |
| 2015/0129781 A1 | 5/2015 | Kretschmann |
| 2015/0148734 A1 | 5/2015 | Fewkes et al. |
| 2015/0150233 A1 | 6/2015 | Dykstra |
| 2015/0182646 A1 | 7/2015 | Anderson et al. |
| 2015/0219308 A1* | 8/2015 | Dross .............. F21V 29/505 362/294 |
| 2015/0233536 A1 | 8/2015 | Krames et al. |
| 2015/0273093 A1 | 10/2015 | Holub |
| 2016/0000950 A1 | 1/2016 | Won |
| 2016/0015840 A1 | 1/2016 | Gordon |
| 2016/0030610 A1 | 2/2016 | Peterson et al. |
| 2016/0091172 A1 | 3/2016 | Wu et al. |
| 2016/0249436 A1 | 8/2016 | Inskeep |
| 2016/0271280 A1 | 9/2016 | Liao et al. |
| 2016/0271281 A1 | 9/2016 | Clynne et al. |
| 2016/0273717 A1 | 9/2016 | Krames et al. |
| 2016/0276550 A1 | 9/2016 | David et al. |
| 2016/0324996 A1 | 11/2016 | Bilenko et al. |
| 2016/0345569 A1 | 12/2016 | Freudenberg et al. |
| 2016/0375161 A1 | 12/2016 | Hawkins et al. |
| 2016/0375162 A1 | 12/2016 | Marry et al. |
| 2016/0375163 A1 | 12/2016 | Hawkins et al. |
| 2017/0014538 A1 | 1/2017 | Rantala |
| 2017/0081874 A1 | 3/2017 | Daniels |
| 2017/0094960 A1 | 4/2017 | Sasaki et al. |
| 2017/0100607 A1 | 4/2017 | Pan et al. |
| 2017/0281812 A1 | 10/2017 | Dobrinsky et al. |
| 2018/0117189 A1 | 5/2018 | Yadav et al. |
| 2018/0117190 A1 | 5/2018 | Bailey |
| 2018/0117193 A1 | 5/2018 | Yadav et al. |
| 2018/0124883 A1 | 5/2018 | Bailey |

FOREIGN PATENT DOCUMENTS

| | | | |
|---|---|---|---|
| CN | 205360038 U | 7/2016 | |
| CN | 106937461 | 7/2017 | |
| DE | 102011001097 A1 | 9/2012 | |
| DE | 102015207999 A1 | 11/2016 | |
| EP | 0306301 A1 | 3/1989 | |
| EP | 1180640 A1 * | 2/2002 | ........... F21V 7/0008 |
| EP | 1693016 A1 | 8/2006 | |
| EP | 1887298 A1 | 2/2008 | |
| EP | 1943880 B1 | 4/2013 | |
| FR | 2773715 A1 | 7/1999 | |
| JP | 2003339845 A | 12/2003 | |
| JP | 2004261595 A | 9/2004 | |
| JP | 2004275927 A | 10/2004 | |
| JP | 2007511279 A | 5/2007 | |
| KR | 20130096965 A | 9/2013 | |
| KR | 101526261 B1 | 6/2015 | |
| KR | 101648216 B1 | 8/2016 | |
| KR | 20160127469 A | 11/2016 | |
| KR | 101799538 B1 | 11/2017 | |
| TW | M530654 U | 10/2016 | |
| WO | 0114012 A1 | 3/2001 | |
| WO | 03037504 A1 | 5/2003 | |
| WO | 03063902 A2 | 8/2003 | |
| WO | 03084601 A2 | 10/2003 | |
| WO | 03089063 A1 | 10/2003 | |
| WO | 2004033028 A2 | 4/2004 | |
| WO | 2005048811 A2 | 6/2005 | |
| WO | 2005049138 A1 | 6/2005 | |
| WO | 2006023100 A1 | 3/2006 | |
| WO | 2006100303 A2 | 9/2006 | |
| WO | 2006126482 A1 | 11/2006 | |
| WO | 2007012875 A1 | 2/2007 | |
| WO | 2007035907 A2 | 3/2007 | |
| WO | 2008071206 A1 | 6/2008 | |
| WO | 2009056838 A1 | 5/2009 | |
| WO | 2010110652 A1 | 9/2010 | |
| WO | 2015066099 A2 | 5/2015 | |
| WO | 2016019029 A1 | 2/2016 | |
| WO | 2017205578 A1 | 11/2017 | |

OTHER PUBLICATIONS

Burkhart, C. N. et al., "Assesment of etiologic agents in acne pathogenesis," Skinmed, 2003, vol. 2, No. 4, pp. 222-228.

Tong, Y., et al. "Population study of atmospheric bacteria at the Fengtai district of Beijing on two representative days," Aerobiologica, 1993, vol. 9, 1 page, Abstract only provided.

Tong, Y. et al., "Solar radiation is shown to select for pigmented bacteria in the ambient outdoor atmosphere," Photochemistry and Photobiology, 1997, val. 65, No. 1, pp. 103-106.

Marshall, J. H., et al., "Pigments of *Staphylococcus au reus*, a series of triterpenoid carotenoids," J. Bacteriology, 1981, vol. 147, No. 3, pp. 900-913.

Pelz, A. et al., "Structure and biosynthesis of staphyloxanthin production of methicillin-resistant *Staphylococcus aureus*," Biol. Pharm. Bull., 2012, val. 35, No. 1, 9 pages.

Sakai, K., et al., "Search for inhibitors of staphyloxanthin production by methicillin-resistant *Staphylococcus aureus*," Biol. Pharm. Bull., 2012, val. 35, No. 1, pp. 48-53.

Clauditz, A. et al., "Staphyloxanthin plays a role in the fitness of *Staphylococcus aureus* and its ability to cope with oxidative stress," Infection and Immunity, 2006, vol. 74, No. 8, 7 pages.

Feng-Chyi Duh et al., "Innovative Design of an Anti-bacterial Shopping Cart Attachment", Journal of Multidisciplinary Engineering Science and Technology (JMEST), Oct. 10, 2015, vol. 2 Issue 10, http://www.jmest.org/wp-content/uploads/JMESTN42351112.pdf.

Drew Prindle, "This UV-Emitting Door Handle Neutralizes Bacteria, Helps Fight the Spread of Disease", Digital Trends, Jun. 19, 2015, https://www.digitaltrends.com/cool-tech/uv-door-handle-kills-germs/.

Jun. 29, 2018—(DE) Office Action—App 112016003453.9.

Apr. 19, 2018—U.S. Non-Final Office Action—U.S. Appl. No. 15/886,366.

Kundrapu et al. "Daily disinfection of high touch surfaces in isolation rooms to reduce contamination of healthcare workers' hands". Journal of Infection Control and Hospital Epidemiology; vol. 33, No. 10, pp. 1039-1042, published Oct. 2012.

Sofia Pitt and Andy Rothman, "Bright idea aims to minimize hospital-acquired infections", CNBC News website, published on Dec. 9, 2014 and retrieved from website: https://www.cnbc.com/2014/12/09/bright-idea-aims-to-minimize-hospital-acquired-infections.html. 6 pages.

Sarah Ward, "LED Retrofit Health ROI? See VitalVio", Poplar Network website, published on Aug. 13, 2014 and retrieved from website: https://www.poplarnetwork.com/news/led-retrofit-health-roi-see-vitalvio. 3 pages.

International Search Report and Written Opinion issued in connection with corresponding PCT application PCT/US17/68749 dated Mar. 6, 2018.

International Search Report and Written Opinion for corresponding International Application No. PCT/US17/68755 dated Apr. 16, 2018, 17 pages.

Wang, Shun-Chung, et al.; "High-Power-Factor Electronic Ballast With Intelligent Energy-Saving Control for Ultraviolet Drinking-

(56) References Cited

OTHER PUBLICATIONS

Waler Treatment Systems"; IEEE Transactions on Industrial Electronics; vol. 55; Issue 1; Date of Publication Jan. 4, 2008; Publisher IEEE.
Berezow Alex, How to Kill Insects With Visible Light, Real Clear Science, Jan. 11, 2015, pp. 1-4, <https://www.realclearscience.com/journal_club/2015/01/12/how_to_kill_insects_with_visible_light_109021.html>.
Hori Masatoshi et al., Lethal Effects of Short-Wavelength Visible Light on Insects, Scientific Reports, Dec. 9, 2014, pp. 1-6, Graduate School of Agricultural Science, Tohoku University, Sendai, Japan. <https://www.semanticscholar.org/paper/Lethal-effects-of-short-wavelength-visible-light-o-Hori-Shibuya/2c11cb3f70a059a051d8ed02fff0e8a967a4c4d4>.
Master Blaster, Tohoku University Team Discovers Blue Light is Effect at Killing Insects, Sora News 24, Dec. 12, 2014, pp. 1-5, Japan, <https://en.rocketnews24.com/2014/12/12/tohoku-university-team-discovers-blue-light-is-effective-at-killing-insects/>.
Jul. 19, 2018—U.S. Final Office Action—U.S. Appl. No. 15/856,971.
Oct. 1, 2018—U.S. Advisory Action—U.S. Appl. No. 15/856,971.
Jul. 17, 2018—U.S. Final Office Action—U.S. Appl. No. 15/857,128.
Oct. 1, 2018—U.S. Advisory Action—U.S. Appl. No. 15/857,128.
Sep. 13, 2018—U.S. Non-Final Office Action—U.S. Appl. No. 15/940,127.
Nov. 1, 2018—U.S. Final Office Action—U.S. Appl. No. 15/886,366.
Nov. 15, 2018—U.S. Non-Final Office Action—U.S. Appl. No. 16/000,690.
Dec. 3, 2018—U.S. Restriction Requirement—U.S. Appl. No. 15/856,971.
Dec. 3, 2018—U.S. Non-Final Office Action—U.S. Appl. No. 15/857,128.
Dornob, "Healthy Handle: Self-Sanitizing UV Dorr Knob Kils Germs", Dornob.com, Dec. 5, 2018, pp. 1-3, https://dornob.com/healthy-handle-self-sanitizing-uv-door-knob-kills-germs/.
Kickstarter, "Orb, The World's First Germ-Killing BLue/UV Light Ball", Dec. 10, 2018, pp. 1-10,<https://www.kickstarter.com/projects/572050089078660/orbtm-the-worlds-first-germ-killing-uv-light-ball>.
Nutone, "QTNLEDB LunAura Collection 110 CFM Fan,Light,LED Nightlight, with Tinted Light Panel, Energy Star® Certified Ventilation Fans", Dec. 11, 2018, p. 1, http://www.nutone.com/products/product/a6da75af-8449-4d4d-8195-7011ce977809.
Nutone, "NuTone Bath and Ventilation Fans", Dec. 11, 2018, pp. 1-2, http://www.nutone.com/products/filter/qt-series-fanlights-25a05450-d47b-4ab8-9992-f8c2cd3t7b90.
Nutone, "Ultra Pro™ Series Single-Speed Fans and Fan/Lights", Dec. 11, 2018, p. 1, http://www.nutone.com/products/filter/ultra-pro-series-fanlights-eb590f89-dca2-40e7-af39-06e4cccb96ca.
Dec. 12, 2018—U.S. Final Office Action—U.S. Appl. No. 15/886,420.
Dai et al., "Blue light for infectious diseases: Propionibacterium acnes, Helicobacter pylori, and beyond?," Drug Resist Update, 15(4): 223-236 {Aug. 2012).
Halstead et al., "The antibacterial activity of blue light against nosocomial wound pathogens growing planktonically and as mature biofilms," Appl. Environ, Microbial., Apr. 2016, 38 pages, retrieved from: http://aem.asm.org/.
R.S. McDonald et al., "405 nm Light Exposure of Osteoblasts and Inactivation of Bacterial Isolates From Arthroplasty Patients: Potential for New Disinfection Applications?," European Cells and Materials vol. 25, (2013), pp. 204-214.
Tomb et al., "Inactivation of Streptomyces phage C31 by 405 nm light," Bacteriophage, 4:3, Jul. 2014, retrieved from: http://dx.doi.org/10.4161/bact.32129, 7 pages.
Tsukada et al., "Bactericidal Action of Photo-Irradiated Aqueous Extracts from the Residue of Crushed Grapes from Winemaking," Biocontrol Science, vol. 21, No. 2, (2016), pp. 113-121, retrieved from: https://lwww.researchgate.net/publication/304628914.
International Search Report and Written Opinion issued in connection with corresponding PCT Application No. PCT/US2016/036704 dated Dec. 8, 2016, 20 pages.
LEDs Magazine, "Lumination Vio LED combines 405 nm chip with new phosphors," retrieved from the Internet on Apr. 20, 2017 at: http://www.leds.magazine.com/articles/2007/06/lumination-vio-led-combines-405-nm-chip-with-new-phosphors.html, Published Jun. 14, 2007, 2 pages.
LEDs Magazine, "ANSI evaluates revisions to SSL chromaticity standard," retrieved from the Internet on Apr. 20, 2017 at: http://www .ledsmagazine.com/articles/2011/07/ansi-evaluates-revisions-to-ssl-chromaticity-standard-magazine.html, Published Jul. 18, 2011, 4 pages.
LEDs Magazine, "ANSI works to update the solid-state lighting standard for chromaticity," retrieved from the Internet on Apr. 20, 2017 at: http://www.ledsmagazine.com/articles/print/volume-12/issue-2/features/standards/ansi-works-to-update-the-ssl-chromaticity-standard.html, Published Feb. 23, 2015, 5 pages.
LEDs Magazine, "ANSI continues advancements on SSL chromaticity standard," retrieved from the Internet on Apr. 20, 2017 at: http/lwww.ledsmagazine.com/articles/print/volume-12/issue-11/features/standards/ansi-continues-advancements-on-ssl-chromaticity-standard.html, Published Dec. 8, 2015, 6 pages.
Soraa, "PAR30L," retrieved from the Internet on Apr. 20, 2017 at: http://www_soraa.com/products/22-PAR30L, 6 pages.
Soraa, "PAR30L 18.5W," retrieved from the Internet on Apr. 20, 2017 at: http://wwvv.soraa.com/products, 5 pages.
Bache et al., "Clinical studies of the High-Intensity Narrow-Spectrum light Environmental Decontamination System (HINS-light EDS), for continuous disinfection in the burn unit inpatient and outpatient settings," Burns 38 (2012), pp. 69-76.
Patent Cooperation Treaty, Search Report—Written Opinion, International Application No. PCT/US16/44634, dated Oct. 20, 2016, 14 pages.
Color Phenomena, "CIE-1931 Chromaticity Diagram," last updated Aug. 22, 2013, retrieved from www.color-theory-phenomena.nl/10.02.htm on Jan. 20, 2016, 3 pages.
Patent Cooperation Treaty, Written Opinion of the International Searching Authority and International Search Report for PCT/US2015/042678 dated Nov. 20, 2015, 13 pages.
Patent Cooperation Treaty, International Preliminary Report on Patentability for PCT/GB2008/003679 dated May 4, 2010, 9 pages.
Patent Cooperation Treaty, Written Opinion of the International Searching Authority and International Search Report for PCT/GB2008/003679 dated Oct. 31, 2008, 11 pages.
U.S. Appl. No. 15/886,420, Office Action dated May 9, 2018, 9 pages.
U.S. Appl. No. 15/223,134, Third Party Submission submitted Jun. 6, 2017, 25 pages.
Yi, Notice of Allowance and Fee(s) due for U.S. Appl. No. 14/501,931 dated Jan. 20, 2016, 8 pages.
Yu, J. et al., "Efficient Visible-Light-Induced Photocatalytic Disinfection on Sulfur-Doped Nanocrystalline Titania," Environ. Sic. Technol., 39, 2005, pp. 1175-1179.
Demidova, T. et al., "Photodynamic Therapy Targeted to Pathogens," International Journal of Immunipathology and Pharmacology, 17(3), pp. 245-254, 2004.
Ashkenazi, H. et al., "Eradication of Propionibacterium acnes by its endogenic porphyrins after illumination with high intensity blue light," FEMS Immunology and Medical Microbiology, 35, pp. 17-24, 2003.
Elman, M. et al., "The Effective Treatment of Acne Vulgaris by a High-intensity, Narrow Band 405-420 nm Light Source," Cosmetic & Laser Ther, 5, pp. 111-116, 2003.
Sikora, A. et al., "Lethality of visable light for *Escherichia coli*hemH 1 mutants influence of defects in DNA repair," DNA Repair, 2, pp. 61-71, 2003.
Huffman, D. et al., "Inactivation of Bacteria, Virus and Cryptospordium by a Point-of-use Device Using Pulsed Broad Spectrum White Light," Wat. Res. 34(9), pp. 2491-2498, 2000.
Papageorgiou, P. et al., "Phototherapy with Blue (415 nm) and Red (660 nm) Light in the Treatment of Acne Vulgaris," British Journal of Dermatology, 2000, pp. 973-978.
Burchard, R. et al., "Action Spectrum for Carotenogenesis in Myxococcus xanthus," Journal of Bateriology, 97(3), 1969, pp. 1165-1168.

(56) References Cited

OTHER PUBLICATIONS

Wainwright, "Photobacterial activity of phenothiazinium dyes against methicillin-resistant strains of *Staphylococcus aureus*," Oxford University Press Journals, retrieved from: http://dx.doi.org/10.1111/j.1574-6968.1998.tb12908.x on Jul. 23, 2015, 8 pages.
Yoshimura et al., "Antimicrobial effects of phototherapy and photochemotherapy in vivo and in vitro," British Journal of Dermatology, 1996, 135: 528-532.
Wilson et al., "Killing of methicillin-resistant *Staphylococcus aureus* by low-power laser light," J. Med, Microbial., vol. 42 (1995), pp. 62-66.
Kawada et al.,"Acne Phototherapy with a high-intensity, enhanced, narrow-band, blue light source: an open study and in vitro investigation," Journal of Dermatological Science 30 (2002) pp. 129-135.
Maclean et al., "High-intensity narrow-spectrum light inactivation and wavelength sensitivity of *Staphylococcus auresu*," FEMS Microbial. Lett., vol. 285 (2008) pp. 227-232.
Reed, "The History of Ultraviolet Germicidal Irradiation for Air Disinfection," Public Health Reports, Jan.-Feb. 2010, vol. 125, 13 pages.
Ward, "Experiments on the Action of Light on Bacillus anthracis," Received Dec. 15, 1892, 10 pages.
Hamblin et al., "Helicobacter pylori Accumulates Photoactive Porphyrins and Is Killed by Visable Light," Antimicrobial Agents and Chemotherapy, Jul. 2005, pp. 2822-2827.
Dai et al., "Blue Light Rescues Mice from Potentially Fatal Pseudomonas aeruginosa Burn Infection: Efficacy, Safety, and Mechanism of Action," Antimicrobial Agents and Chemotherapy, Mar. 2013, vol. 57{3}, pp. 1238-1245.
Holzman, "405-nm Light Proves Potent at Decontaminating Bacterial Pathogens," retrieved from: http://forms.asm.org/microbe/index.asp?bid=64254 on Aug. 6, 2015, 34 pages.
Guffey et al., "In Vitro Bactericidal Effects of 405-nm and 470-nm Blue Light," Photomedicine and Laser Surgery, vol. 24, No. 6, retrieved from: https:/lwww.liebertpub.com/doi/abs/10.1089/pho.2006.24.684 on Mar. 23, 2018, 2 pages, abstract only provided.
Kristoff et al., "Loss of photoreversibility for UV mutation in *E. coli* using 405 nm or near-US challenge," Mutat Res., May 1983, 109{2}: 143-153, 2 pages, abstract only provided.
Turner et al., "Comparative Mutagenesis and Interaction Between Near-Ultraviolet {313- to 405-nm) and Far-Ultraviolet 254-nm) Radiation in *Escherichia coli* Strains with Differeing Repair Capabilities," Journal of Bacteriology, Aug. 1981 , pp. 410-417.
Knowles et al., "Near-Ultraviolet Mutagenesis in Superoxide Dismutase-deficient Strains of *Escherichia coli*," Environmental Health Perspectives, vol. 102{1), Jan. 1994, pp. 88-94.
Jagger, "Photoreactivation and Photoprotection," Photochemistry and Photobiology, vol. 3, Issue 4, Dec. 1964, retrieved from: https://onlinelibrary.wiley.com/doi/abs/10.1111/j.1751-1097.1964.tb08166.x on Mar. 23, 2018, 4 pages, abstract only provided.
Chukuka et al., Visible 405 nm SLD light photo-destroys metchicillin-resistant *Staphylococcus aureus* {MRSA) in vitro, Lasers in Surgery and Medicine, vol. 40, Issue 10, Dec. 8, 2008, retrieved from: https://onlinelibrary.wiley.com/doi/abs/10.1002/lsm.20724 on Mar. 23, 2018, 4 pages, abstract only provided.
Bek-Thomsen, M., "Acne is Not Associated with Yet-Uncultured Bacteria," J. Clinical Microbial., 2008, 46{10), 9 pages.
Harrison, A.P., "Survival of Bacteria," Annu. Rev. Microbial, 1967, p. 143, vol. 21.
Feuerstein et al., "Phototoxic Effect of Visible Light on Porphyromonas gingivalis and Fusobacterium nucleatum: An In Vitro Study," Photochemistry and Photobiology, vol. 80, Issue 3, Apr. 30, 2007, retrieved from: https://onlinelibrary.wiley.com/doi/abs/10.1111/j.1751-1097.2004.tb00106.x on Mar. 23, 2018, abstract only.
Pochi, P.E., "Acne: Androgens and microbiology," Drug Dev, Res., 1988, val. 13, 4 pages, abstract only provided.
Burkhart, C. G. et al., "Acne: a review of immunologic and microbiologic factors," Postgraduate Medical Journal, 1999, vol. 75, pp. 328-331.
Feb. 28, 2019—(WO) International Search Report—App PCT/US2018/061843.
Feb. 28, 2019—(WO) International Search Report—App PCT/US2018/061856.
Feb. 11, 2019—(WO) International Search Report—App PCT/US2018/061859.
Jan. 9, 2019—U.S. Notice of Allowance amd Fee(s) Due—U.S. Appl. No. 15/940,127.
Jan. 4, 2019—Taiwan Office Action—ROC (Taiwan) Pat. Appl. No. 104124977.

* cited by examiner

LIGHT DIRECTING ELEMENT

CROSS REFERENCE TO RELATED APPLICATIONS

This patent claims the benefit of U.S. Provisional Patent Application No. 62/594,802 filed Dec. 5, 2017 and entitled "Light Directing Element with Internal Diffuser and Related Method," which is hereby incorporated herein by reference in its entirety.

BACKGROUND

Aspects of the present disclosure relate to light directing elements, and more specifically, to light directing elements with internal diffusers and methods of producing the light directing elements.

Internal illumination of elements may be used to create aesthetically pleasing lighting to illuminate dark areas for safety and/or to draw attention to objects. The materials used to make an internally illuminated element may distort and/or diffract light in such a way that it does not exit the element in an efficient, consistent, or more uniform manner thereby effecting the intensity or irradiance on an exterior surface of the element.

SUMMARY

An example light directing element may comprise an elongated body having a first end, a second end and an exterior surface, the elongated body being transparent or translucent to permit transmission of light axially and radially therethrough, a light emitter disposed at the first end of the elongated body, and a diffuser including at least one reflective element disposed within the elongated body, wherein the diffuser is configured to redirect light emitted from the light emitter towards the exterior surface and wherein the diffuser expands in cross-section towards the second end.

An example light directing element may comprise a transparent or translucent body having a first end, a second end and an exterior surface, and a diffuser disposed within the transparent or translucent body and expanding in cross-section towards the second end, wherein the diffuser comprises at least one reflective element configured to redirect light axially transmitted from the first end radially towards the exterior surface.

An example method may comprise casting a conically shaped diffuser comprising at least one alignment pin, inserting the at least one alignment pin into a first plate, inserting a tube into the first plate surrounding the conically shaped reflective diffuser, and filling the tube with casting material.

The foregoing and other features of the disclosure will be apparent from the following more particular description of examples of the disclosure.

BRIEF DESCRIPTION OF THE DRAWINGS

The examples of this disclosure will be described in detail, with reference to the following figures, wherein like designations denote like elements, and wherein.

It is noted that the drawings of the disclosure are not to scale. The drawings are intended to depict only example aspects of the disclosure, and therefore should not be considered as limiting the scope of the disclosure. In the drawings, like numbering may represent like elements.

DETAILED DESCRIPTION

Figure 1A:
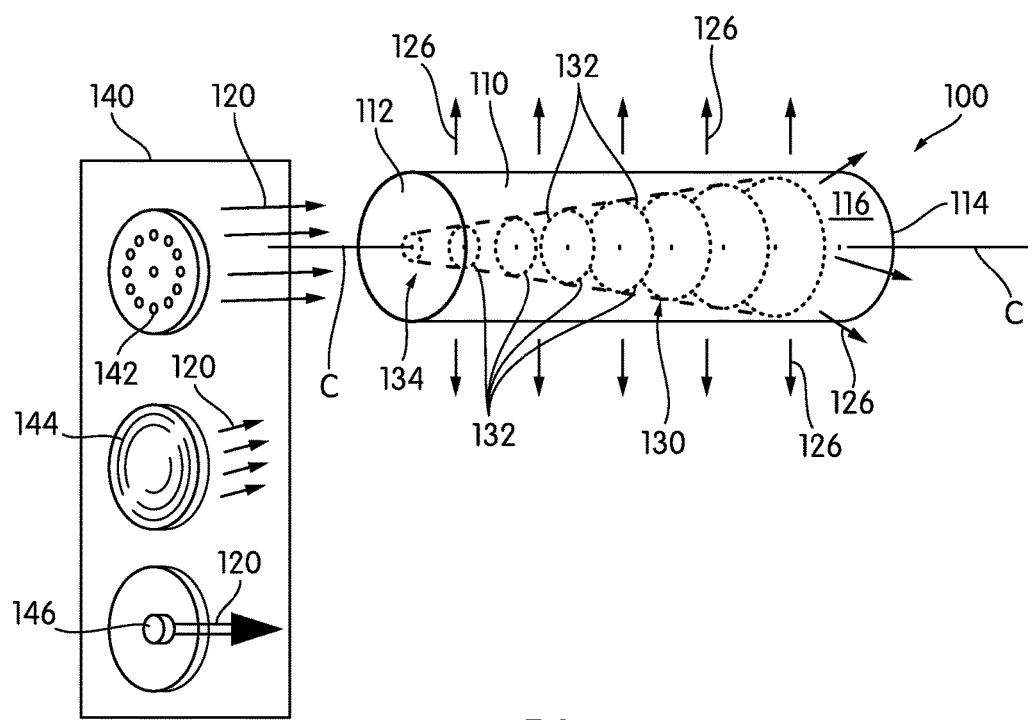
FIGS. 1A-1B show perspective views of light directing elements according to example systems, methods, and apparatuses of the disclosure.

High touch surfaces may be commonly inhabited by harmful microorganisms due to the nature of their use by humans or other animals. Microorganisms may transfer from, e.g., human to human, through contact of the same high touch surfaces and can cause illness to the users. Harmful bacteria such as *Escherichia coli* (*E. coli*), *Salmonella*, Methicillin-resistant *Staphylococcus Aureus* (MRSA), and *Clostridium Difficile* may be found on many surfaces, which may increase the chance of a user becoming sick or transmitting the bacteria. For example, there are numerous cases of hospital acquired bacterial infections. Healthcare facilities are one or many facilities at risk for causing or spreading illness. Athletic facilities/gyms, public transportation vehicles, food preparation or production plants, hotels, offices, etc., are all at risk for hosting the contraction of bacterial related illnesses by their inhabitants.

High touch surfaces, such as handles, may be disinfected in a number of ways, such as cleaning with disinfecting, chemical cleaners. Chemical cleaners may only provide intermittent disinfection, and may allow harmful microorganisms to build up between cleanings. Because humans may contact a surface at any time, continuous disinfection may be advantageous.

In some examples, antimicrobial coatings such as silver, copper or zinc, may be used to disinfect. These coatings may be applied directly to surfaces, or may be provided in high touch surfaces (e.g., handles). These coatings, however, may wear off or may require replenishing. They may also be messy and/or unsafe for human contact. Antimicrobial coatings may also damage surfaces to which they are applied.

In some examples, high touch surfaces may be internally illuminated. Often, internal illuminated surfaces may be prone to dead spots (e.g., areas with inconsistent or no illumination) due to various reasons such as spacing of centrally located light emitters, edge lighting decreasing over lengths of surfaces, etc. Examples of the present disclosure provide expansive light directing elements to redirect light from a light source to consistently illuminate a surface with a similar intensity and irradiance. In examples disclosed herein, internal illuminations may be configured with disinfecting properties. In contrast to devices that transmit ultraviolet (UV) light through a high touch surface for disinfection, which may be harmful to humans and so the light must be off during human use, examples disclosed herein provide non-harmful disinfecting internal illumination to initiate inactivation of bacteria on external surfaces. In such examples, the internal lighting may be continuously illuminated to constantly inactivate bacteria while being safe for human exposure.

The example light directing elements may include an elongated body having a first end, a second end, and an exterior surface. The example light directing elements may be transparent or translucent to permit transmission of light therethrough. The example light directing elements may be solid and/or cylindrical, and may be used as high touch surfaces (e.g., handles). In some examples, the light directing elements may have various cross sections other than circular (e.g., from a cylinder) such as, for example, a square cross section, a polynomial cross section, a D shaped cross section, an ovular cross section, etc. Further, the example light directing elements may be internally illuminated with disinfecting light. The light may be any color desired. In contrast to conventional systems that employ dangerous (UV) light, light directing elements may direct light through the exterior surface, wherein at least a portion of the light exiting the exterior surface has a wavelength in a range of approximately 380 to approximately 420 nanometers (nm). In some examples, the light directing elements may be configured such that a portion of light exiting the exterior surfaces of the light directing elements has a wavelength of 405 nm. Light having a wavelength in the range of approximately 380 to approximately 420 nm may inactivate microorganisms such as, for example, *Escherichia coli* (*E. coli*), *Salmonella*, Methicillin-resistant *Staphylococcus Aureus* (MRSA), *Clostridium Difficile*, and a wide variety of yeasts and/or fungi. The disinfecting light may also include other wavelengths of light to create other colors such as, for example, white light.

The example light directing elements may enable the direction and distribution of light to their exterior surfaces with sufficient intensity and/or irradiance to consistently illuminate the light directing element. In examples utilizing disinfecting light, the light should have sufficient intensity and/or irradiance to disinfect the exterior surface (e.g., achieving continual and even disinfection).

To this end, an example light directing element may include a diffuser including at least one light reflective element arranged within the elongated body to create an axially, enlarging reflective arrangement to progressively redirect light toward the exterior surface as the light passes axially through the elongated body. A light emitter may be operably coupled to the elongated body for emitting light axially through the elongated body. The diffuser may provide a mechanism to direct and distribute lighting in a controlled, consistent, and uniform manner to an exterior surface of the elongated body.

Figure 1B:
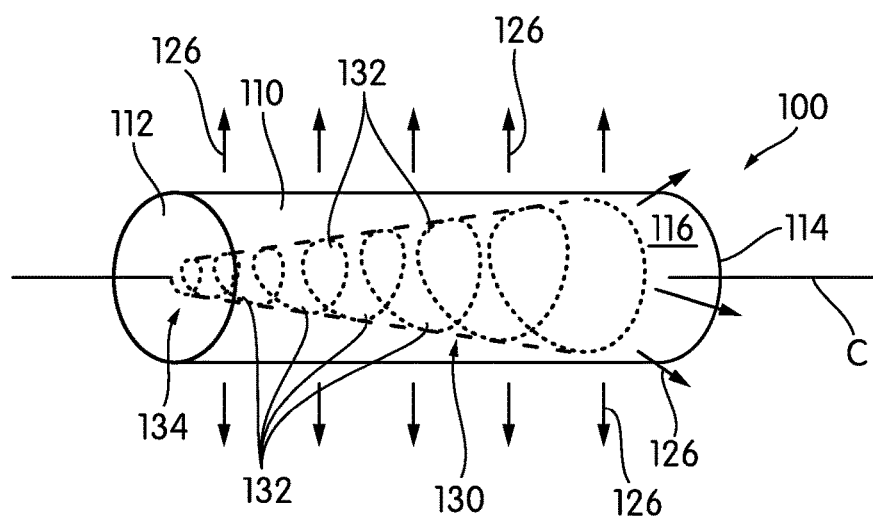
Figure 2:
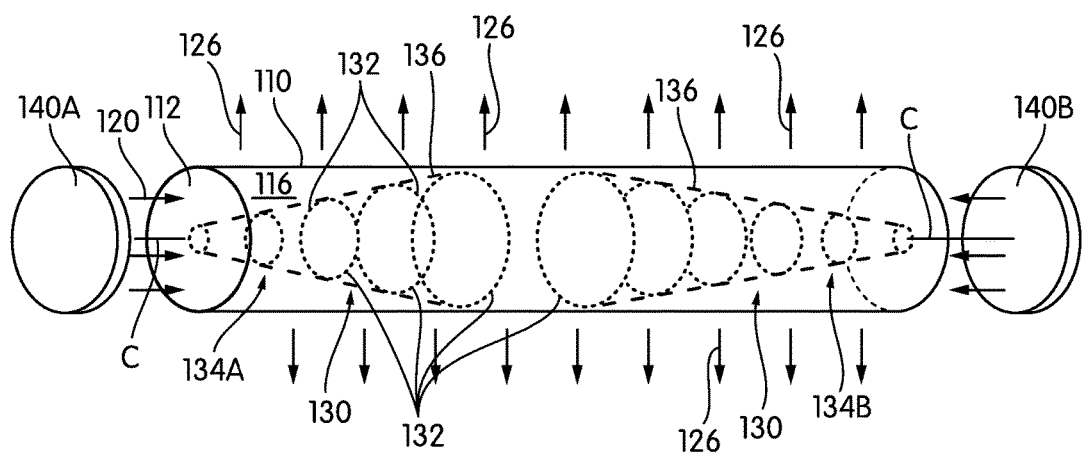
FIG. 2 shows a perspective view of a light directing element according to example systems, methods, and apparatuses of the disclosure.

Referring to the drawings, FIGS. 1A, 1B, and 2 show perspective views of an example light directing element 100 (hereinafter "element 100"). Element 100 may include an elongated body 110 having a first end 112, a second end 114, and an exterior surface 116. Elongated body 110 may be transparent or translucent to permit transmission of light 120 therethrough (e.g., from one end to the other end, out the exterior surface, etc.). Light 120 may travel through elongated body 110 regardless of where light 120 originates.

Elongated body 110 may be used as any internally illuminated element, such as a lighting element, but may further be utilized as a high touch surface, such as a handle. A "high touch" surface may be an outside part or uppermost layer of something (e.g., body 110) that may be (but not necessarily) exposed to contact (e.g., by humans or other animals) that transfers or otherwise creates microorganisms on that part or layer. Element 100 may be utilized as a handle frequently grasped by users, e.g., a door handle, refrigerator handle, etc.

Elongated body 110 may also include an exterior surface 116 configured to be illuminated, grasped, and/or disinfected. Exterior surface 116 may be is textured or otherwise diffuse and may replace a preexisting high touch surface as the outside part or layer of a structure. A portion of elongated body 110 (not shown) through which the transmission of light 120 may not be necessary (e.g., such as those portions covered by end caps or transfer caps shown and described with reference to FIGS. 22-23) may not need to be transparent or translucent. Elongated body 110 can be made of any transparent or translucent material, e.g., clear acrylic, diffuse polycarbonate plastic, glass, any combination thereof, etc. "Transparent" or "translucent" may indicate any level of light transmission short of opaque. As shown in FIG. 1A, elongated body 100 may be a solid cylindrical body. However, elongated body 110 may be other shapes that allow for the transmission of light 120 therethrough and to external surface 116, e.g., cylindrical but with one or more planar chords therein, hexagonal, etc.

Element 100 may also include a diffuser 130 including at least one light reflective element 132. In some examples, the diffuser 130 may comprise a plurality of light reflective elements 132 (shown as dots in FIGS. 1 and 2) arranged within elongated body 110 to collectively create at least one axially, enlarging reflective array 134 to progressively redirect light 120 toward exterior surface 116 as light 120 passes axially through elongated body 110. In some examples, the diffuser 130 may be a solid conical structure such as, for example, diffuser 1100 illustrated in FIG. 11. Of course, other shapes may be used such as, for example, a truncated cone, a trapezoidal prism, a paraboloid, a half sphere, a pyramid, other known geometric shapes, and/or any combination thereof.

The plurality of light reflective elements 132 may be arranged within elongated body 110 to redirect light 120 toward exterior surface 116, creating exiting light 126. In some examples, exiting light 126 is substantially uniform and/or comprises a consistent irradiance across a surface area of exterior surface 116. In one example, exiting light 126 may have an irradiance of at least 0.01-0.02 milliWatts per square centimeter ($mW/cm^2$) across exterior surface 116. One or more of the plurality of light reflecting elements 132 may be at least partially reflective so as to redirect light from an incident angle to a reflected angle, which may direct light 120 to exterior surface 116. One or more of the plurality of light reflecting elements 132 may include a planar, magnetic body to allow for proper positioning thereof during manufacture, which will be described in detail herein. One or more of the plurality of light reflective elements 132 may have a magnetic field configured to enable magnetic positioning of the one or more of the plurality of light reflective elements 132 in a desired location within the elongated body 110, such as, e.g., in groups and axially symmetrical about centerline C, helically as shown in FIG. 1B, and/or other configurations. One or more of the plurality of light reflecting elements 132 may be made of, for example, ferromagnetic material, magnetic metal, or include such material. The size of light reflecting elements 132 may vary to better provide uniform and/or consistent illumination across the exterior surface 116. In some examples, one or more of the plurality of light reflecting elements 132 may have a surface area of less than approximately 4 square millimeters (4 $mm^2$).

FIGS. 1A-1B illustrate an example single axially enlarging reflective array 134. As illustrated in FIGS. 1A-1B, the example axially enlarging reflective array 134 may face the first end 112 of the elongated body 110 and may redirect light 120 entering first end 112. FIG. 2 illustrates an example of the elongated body 110 comprising a pair of axially enlarging reflective arrays 134A, 134B. Array 134A may face the first end 112 of the elongated body 110 and may redirect light 120 entering the first end 122. Array 134B may face the second end 114 of elongated body 110 and may redirect light 120 entering the second end 114. An array may face a direction such that reflective portions of reflective elements 132 are positioned to have light from that direction strike them and be redirected. In some examples, the array(s) 134 may be conical in arrangement, such that the apex of the conical arrangement may be closest to the end 112 and/or 114 which it faces. The density and/or position of one or more of the plurality of light reflecting elements 132 may vary axially and/or radially, such that a collimated beam of light 120 oriented parallel to centerline C entering an end 112, 114 of element 100 at an axial position may be output at a correlated radial position. The sum effect of the numerous small reflective elements 132 and exterior surface 116 boundary may create an optic that receives light 120 input on one and/or both ends, and advantageously emits exiting light 126 uniformly over at least a portion of exterior surface 116.

Figure 3:
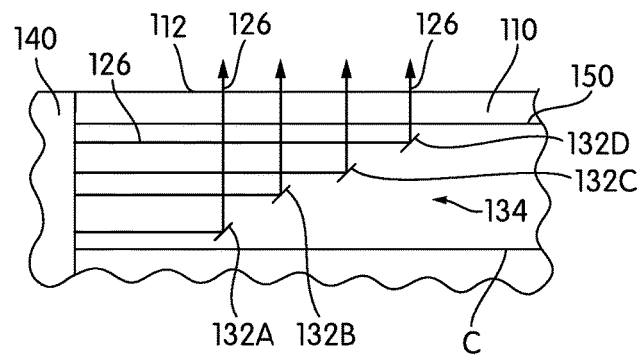
FIG. 3 shows an enlarged cross-section view of a light directing element according to example systems, methods, and apparatuses of the disclosure.
Figure 4:
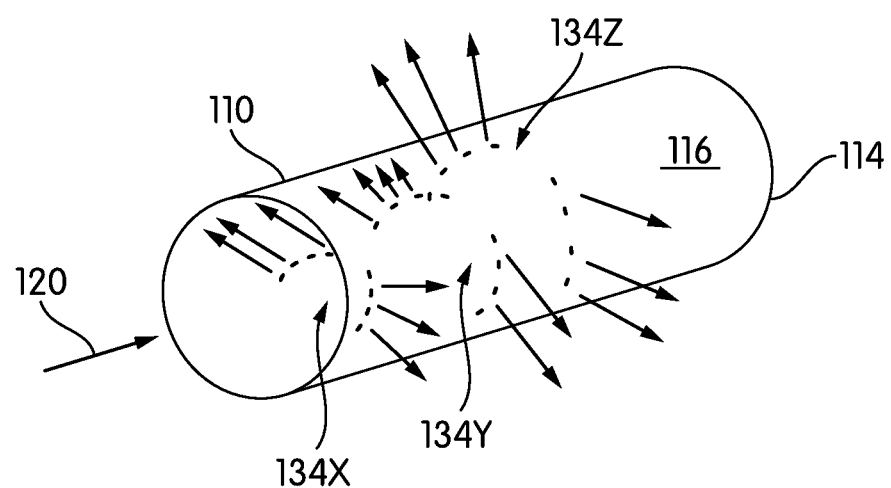
FIG. 4 shows a perspective view of a light directing element according to other example systems, methods, and apparatuses of the disclosure.
Figure 5:
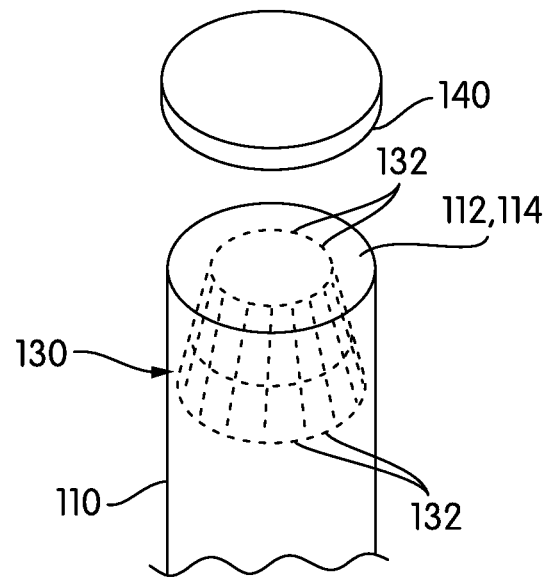
FIG. 5 shows a perspective view of a light directing element according to other example systems, methods, and apparatuses of the disclosure.

As shown in FIGS. 1A and 2, and in an enlarged cross-sectional view of FIG. 3, each axially enlarging reflective array 134 may include one or more groups of light reflective elements 132, which may collectively form a series of increasing sized reflective structures relative to centerline C. In FIGS. 1A and 2, the reflective structures may be circular, e.g., reflective elements 132 may be arranged serially in circles. However, as shown in FIG. 4, reflective array groups 134X, 134Y, 134Z may be arranged as increasing radius arcs, which may not create exiting light 126 entirely about exterior surface 116, but only in selected arcuate sections thereof. Any angle of arc may be employed, e.g., anywhere between 1° and 360°. The example reflective elements may be arranged in a generally conical arrangement. However, as shown in the perspective view of FIG. 5, they may be alternatively arranged in a truncated or frusto-conical arrangement, e.g., conical with a cut off end. Furthermore, the plurality of reflective elements 132 may be arranged in a helical pattern (e.g., FIG. 1B) or may form a solid conical structure (e.g., FIGS. 11-23).

Figure 6:
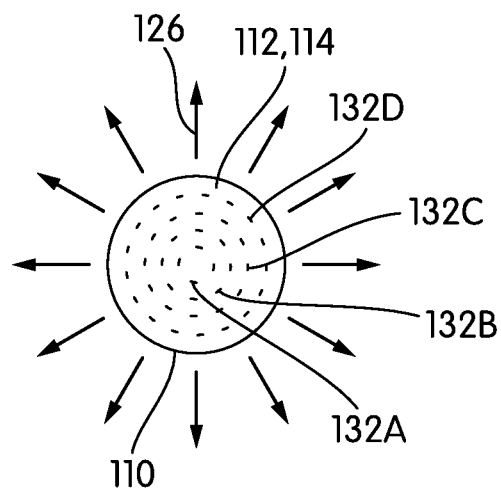
FIG. 6 shows an end view of the light directing element of FIG. 1A or FIG. 2.

As illustrated in FIG. 3, groups of light reflective elements 132 may collectively form a series of increasing sized reflective structures, e.g., circles, to sequentially redirect light 120 along a length of elongated body 110. One or more rays of light 120 entering near a centerline C of elongated body 110 may strike a first group of reflective elements 132A nearest a respective end 112 and may be redirected toward exterior surface 116. One or more rays of light 120 slightly farther from centerline C may strike a second group of reflective elements 132B (e.g., with a larger radius), which may be positioned slightly farther into elongated body 110. The one or more rays of light 120 that strike reflective elements 132B may be redirected toward exterior surface 116. Any number of groups of reflective elements 132 (e.g., 134C, 134D, etc.) may be provided along a length of elongated body at various intervals to enable a uniform or near uniform illumination of exterior surface 116. As illustrated in FIGS. 2-3, each axially enlarging reflective array 134A, 134B may have a progressively decreasing distance from exterior surface 116 as the distance from light emitter 140A, 140B increases. Each array 134A, 134B may be any length of elongated body 110 as desired, e.g., a 50/50 split, a 30/70 split, etc. FIG. 6 shows an end view of elongated body 100 illustrating the groups of reflective elements 132A-132D of FIG. 3 from either end 112 or 114 and the light 126 that is reflected therefrom.

As illustrated in FIG. 1A, light directing element 100 may also include various types of light emitters 140 operably coupled to at least one end 112, 114 of elongated body 110 for emitting light 120 axially into elongated body 110 to strike axially enlarging reflective array(s) 134. As noted, light 120 may eventually exit through exterior surface 116 as exiting light 126. In one example, a single light emitter 140 may be operative to direct light 120 (prior to exiting light 126 exiting exterior surface 116) into first end 112 of elongated body 110, and out exterior surface 116. In another example, two light emitters 140A, 140B may be operably coupled to respective ends 112, 114 of elongated body 110 for emitting light 120 axially into elongated body 110 to strike each of the pair of axially enlarging reflective arrays 134A, 134B with one array 134A having a respective smaller end facing first end 112 of elongated body 110, and the other array 134B has a respective smaller end facing second end 114 of elongated body 110.

Figure 16:
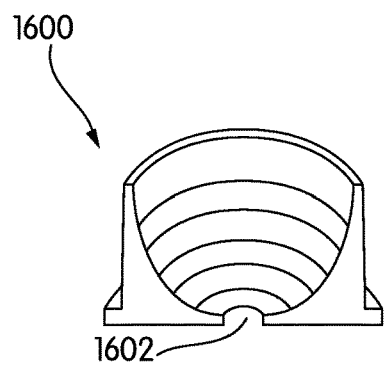
FIG. 16 shows a beam collimator according to example systems, methods, and apparatuses of the disclosure.

Light emitter(s) 140 may include any form of light emission element capable of creating the desired wavelength of light and introducing it to elongated body 110. In some examples, light 120 may enter elongated body parallel with center line C. In some examples, a beam collimator (e.g., as shown in FIG. 16) may be used in connection with light emitter(s) 140 to enable application of collimated rays of light 120. In one example, light emitter 140 may include one or more light emitting diodes (LEDs) 142. LEDs 142 may be coupled to ends 112 and/or 114 via a separate structure or fixedly coupled thereto. Alternatively, LEDs 142 can be embedded within elongated body 110, e.g., within ends 112, 114. In another example, light emitter(s) 140 may include one or more electroluminescent light emitters 144. In another example, light emitter(s) 140 may include one or more lasers 146, e.g., a gallium nitride (GaN) based laser, or a frequency doubling gallium arsenic (GaAs) laser. Light emitter(s) 140 may be part of elongated body 110, or coupled thereto using any now known or later developed coupling process, e.g., adhesive, fasteners, etc.

Light 120 and/or exiting light 126 may have any color desired. In one example, light 120 and exiting light 126 may be any color chosen for illumination and/or aesthetic purposes, e.g., white, green, orange, etc. In some examples, light emitting element 100 may also include a control system operatively coupled to light emitter(s) 140 and/or exiting light 126. The example control system may control operational features such as but not limited to: a duration of illumination, color, light intensity, and/or light irradiance of the light emitter(s) 140 and/or exiting light 126. Control system may include any now known or later developed microcontroller. Light emitting element 100 may also include at least one sensor coupled to control system to provide feedback to control system. Capacitive touch sensors, infrared ("IR") sensors, or piezo electric sensors may be used to detect touch of the exterior surface 1116 (e.g., to change color, intensity, irradiance, etc. based on touch). Similarly, remote cameras and/or occupancy sensors may be used to determine whether exterior surface is likely to be touched (e.g., when a room is vacant there is a low probability that exterior surface will be touched).

The example sensor(s) may sense any parameter of the control environment of light emitting element 100, including but not limited to: touch of light emitting element 100, heat of a user's hand on light emitting element 100, motion of a user, motion of structure to which light emitting element 100 is coupled, temperature, light reception, and/or presence of microorganisms on exterior surface 116, etc. Sensor(s) may include any now known or later developed sensing devices for the desired parameter(s). Control system with (and without) sensor(s) may control operation to be continuous or intermittent based on external stimulus, and depending on the application. In one example, sensor(s) may detect heat/human touch, motion, or light. Sensor(s) may send the detected information to the control system, which may vary the color, intensity, or duration of disinfection of the exiting light 126.

In an example, based on a human touching a surface previously illuminated with 405 nanometer light, a sensor may detect the touch and send information to control system. The control system may then alter the light emitted from the light emitting element to disinfecting white light while in use.

In another example, where light directing element 100 comprises disinfecting properties, exiting light 126 exiting exterior surface 116 may have at least a portion thereof with a wavelength in a range of 380 to 420 nanometers (nm). This wavelength of light may inactivate, decrease, and/or kill microorganisms on surfaces. In one example, exiting light 126 may have at least a portion thereof with a wavelength of 405 nm. Exiting light 126 may solely comprise wavelengths between 380 to 420 nm, or light 120 may be converted in a number of ways, described herein, to create disinfecting light of another color such as white light. In this example, exiting light 126 exiting exterior surface 116 may have any irradiance or intensity sufficient to disinfect exterior surface 116, which may vary depending on, for example: the type of material of body 110, the level of microorganisms thereon, the extent of touching (e.g., low level bedroom door handle versus high level grocery cart handle), the type of application, etc. In one example, exiting light 126 may have an irradiance of at least 0.01-0.02 milliWatts per square centimeter (mW/cm$^2$) across the surface area of exterior surface 116, e.g., all or at least part of exterior surface 116.

The desired exiting light 126 may be created in a number of ways. In one example, light emitter(s) 140 may emit light 120 that is the same as the desired exiting light 126 that exits exterior surface 116 of elongated body 110, e.g., light 120 may simply pass directly out exterior surface 116 as exiting light 126 after being redirected by diffuser 130. In some examples, the color of the exiting light 126 may be selected to match a color of a structure to which the device is attached. In another example, light 120 may be converted prior to exiting exterior surface 116 as exiting light 126 from one color to another color such as white light, or a disinfecting light. For example, light 120 may be converted to a white light having a portion thereof with the wavelength in the range of 380 to 420 nanometers, but also other wavelengths of light to create the white light, e.g., 450-500 nm and 550-700 nm. 450-500 nm light may be produced using one or more blue phosphors and 550-700 nm light may be produced using one or more green and/or red phosphors. In some examples, the red phosphors may be nitride phosphors. Other colors of light may also be similarly generated. In some examples, a multiple LED light emitter may be used to create various colors of light. For example, a multiple LED light emitter may comprise red, green, blue, and violet light emitters configured together for the creation of various colors of light.

In the illustrated example of FIG. 3, elongated body 110 may include a light-converting layer(s) 150 through which light 120 may travel to convert at least a portion of exiting light 126 to a wavelength(s) different from the wavelength of light 120 emitted from light emitter(s) 140. In FIG. 3, light-converting layer 150 may be embedded in elongated body 110; however, it may be located anywhere along a path of light 120 such as on ends 112, 114, or on exterior surface 116. Light-converting layer 150 may include any now known or later developed layer(s) for converting all or certain portion(s) of light 120 to different wavelengths. In some examples, light-converting layer 150 may include at least one phosphor, at least one optical brightener, and/or at least one quantum dot. Light-converting layer 150 may tune light 120 to, for example, alter a color tint of exterior surface 116 or the color tint of the material directly surrounding each of light emitter(s) 140, etc., within device 100. Light-converting layer 150 may be segmented across the layer's surface to convert light 120 to two or more different wavelengths, e.g., one segment to enable some of light 120 to pass unconverted, another segment to convert some of light 120 to another wavelength, and another segment to convert some of light 120 to yet another wavelength. In any event, exiting light 126 may be customized to provide disinfection and/or a desired color. In some examples, exiting light 126 may have a color rendering index (CRI) value of at least 70, a correlated color temperature (CCT) between approximately 2,500 K and 5,000 K and/or a proportion (e.g., between 20% and 44%) of its spectral energy measured in the 380 nm to 420 nm wavelength range.

Figure 7:
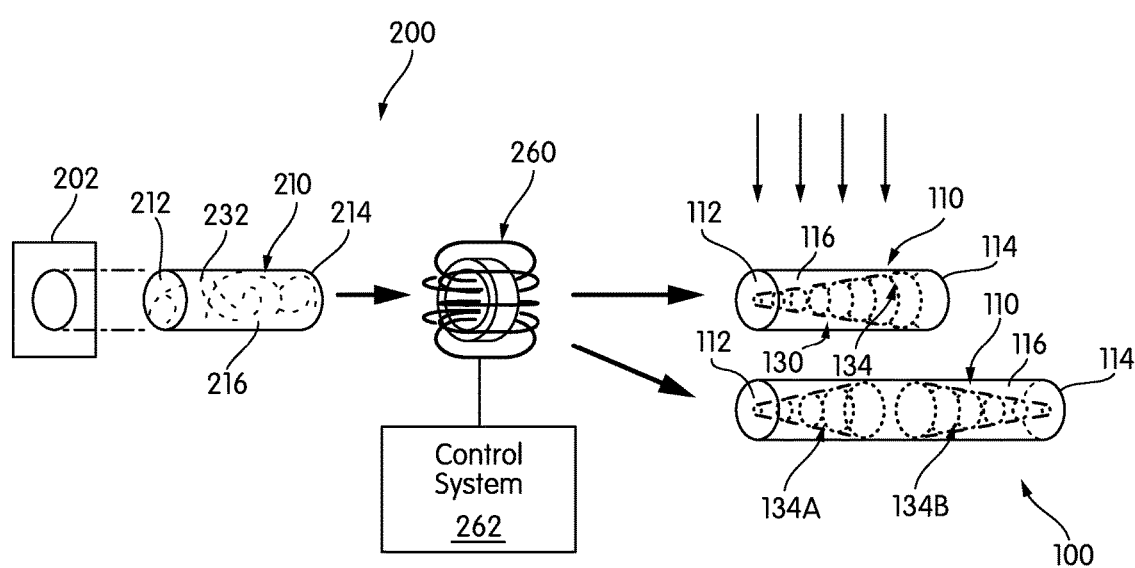
FIG. 7 shows a perspective view of steps of a method according to example systems, methods, and apparatuses of the disclosure.
Figure 8:
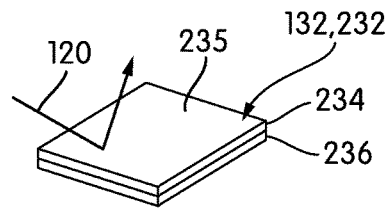
FIG. 8 shows a perspective view of a magnetic light reflective element according to example systems, methods, and apparatuses of the disclosure.

Referring to FIGS. 7-10, a method 200 is illustrated for creating the example light directing element 100. As illustrated in FIG. 7, an extrusion system 202 may extrude a transparent, elongated body 210 having a plurality of magnetic light reflective elements 232 within transparent, elongated body 210. Transparent, elongated body 210 may include a first end 212, a second end 214, and an exterior surface 216. Elongated body 210 may be extruded using any now known or later developed extrusion system 202 capable of forming transparent, elongated body 210 with magnetic light reflective elements 232 therein. Light reflective elements 232 may be dispersed throughout elongated body 210 in any manner, e.g., random, in concentric circles, in a helix, etc. As shown in FIG. 8, one or more magnetic light reflecting element 232 may include, for example, a planar body. One or more magnetic light reflecting element 232 may include a reflective layer 234 having a reflective surface 235, and may include magnetic material (e.g., a ferromagnetic material, mica substrates coated with iron oxides (ferrite) and/or titanium dioxides, or other magnetic material) as another layer 236 or within reflective layer 234. The reflective coating may include one or more dielectric coatings to create a Bragg mirror. Other magnetic pigments that may be employed on other materials may include but are not limited to: iron oxide, and/or titanium oxide. Alternatively, the magnetic material may be a compound featuring at least one of the following elements: iron, aluminum, nickel, cobalt, samarium, dysprosium, or neodymium. One or more of the magnetic light reflecting elements 232 may be subjected to a magnetic field during manufacturing in order to temporarily or permanently magnetize them. In the simplest manifestation, the one or more of the magnetic light reflecting elements 232 may respond to the applied magnetic field, while the material of the elongated body 210 may not. Elongated body 210 may include any now known or later developed transparent material capable of extrusion, e.g., clear acrylic, diffuse polycarbonate plastic, glass, or any combination thereof.

FIG. 7 illustrates that, prior to the transparent, elongated body 210 hardening, a varying electromagnetic (EM) field may be applied along and around at least a portion of transparent, elongated body 210 to arrange a plurality of magnetic light reflective elements 232 within elongated body 210 to collectively create at least one diffuser 130 comprising at least one axially, enlarging reflective array 134 (or arrays 134A, 134B). The varying EM field may be created by an electromagnet system 260 controlled by a control system 262. Control system 262 may include any now known or later developed micro-electronic controller. Elongated body 210 may be passed through a varying EM field created by electromagnet system 260 and controlled by control system 262, which may move and/or manipulate magnetic light reflective elements 232 into groups, a helix, a cone, etc. to form diffuser 130. As the elongated body 210 is extruded into the desired cross section (or shortly thereafter) and remains formable, it may be passed through one or more variable electromagnetic fields (produced by electromagnet system 260). The fields may vary in intensity such that magnetic reflective elements 232 are moved into the desired locations. Control system 262 may also vary the rate of extrusion, temperature, and/or magnetic field strength. In some examples, applying the varying EM field may arrange magnetic light reflective elements 232 to have a progressively decreasing distance from exterior surface 216 as the array extends axially from an end 112, 114 into transparent, elongated body 210. Alternatively, as shown in FIG. 1B, the application of the varying EM field may arrange each axially enlarging reflective array 134 to include an enlarging helical arrangement of magnetic light reflective elements 132. Alternatively, as shown in FIG. 4, the application of the varying EM field may arrange each axially enlarging reflective array 134 to include groups of magnetic light reflective elements 132 collectively forming a series of increasing radius arcs. Applying the varying EM field may arrange magnetic light reflective elements 232 in groups in a series of increasing diameter circles from first end 112 towards the second end 114, or vice versa, from second end 114 towards first end 112, forming at least a portion of a cone configuration 136 (FIG. 1A). As shown in FIGS. 2 and 7, two arrays 134A, 134B may be formed with a first axially enlarging reflective array 134A facing first end 112 of the transparent, elongated body 110 for redirecting light entering first end 112; and a second axially, enlarging reflective array 134B facing second end 114 of transparent, elongated body 110 for redirecting light entering second end 114. Applying the varying EM field may arrange the magnetic light reflective elements 232 within transparent, elongated body 210 to redirect light 120 (e.g., FIG. 3) entering the elongated body toward exterior surface 116 with a substantially uniform irradiance (e.g., 0.01-0.02 mW/cm$^2$) across at least a portion of a surface area of exterior surface 116.

Figure 9:
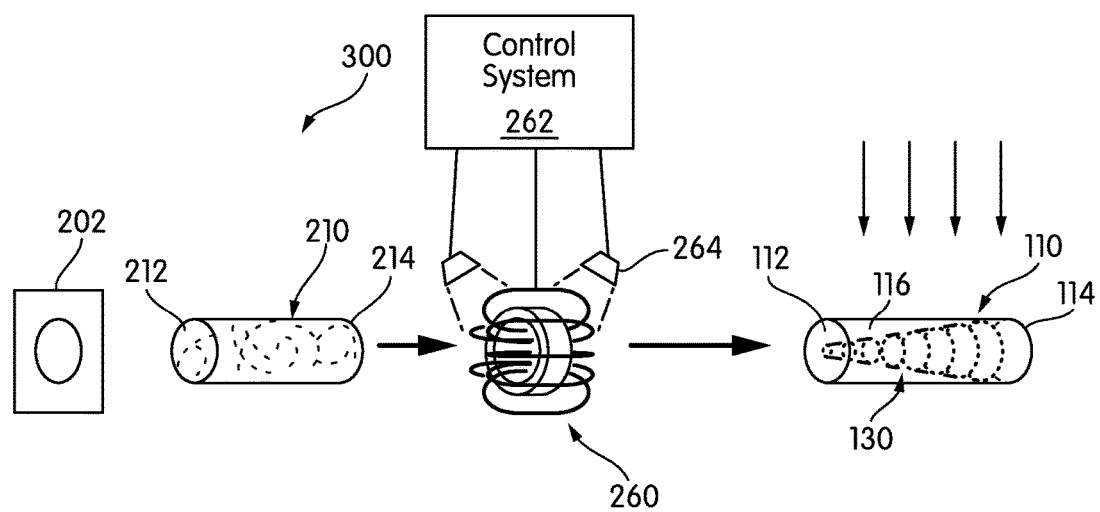
FIG. 9 shows a perspective view of steps of a method according to example systems, methods, and apparatuses of the disclosure.

FIG. 9 illustrates a method 300 for monitoring the arrangement of a plurality of magnetic light reflective elements 232 within transparent, elongated body 210 during the applying the varying EM field, e.g., using a monitoring system 264. Here, similar to FIG. 7, elongated body 210 may be passed through a magnetic field created by electromagnet system 260 and controlled by control system 262 to create a varying EM field that moves and/or manipulates magnetic light reflective elements 232 into groups and form diffuser 130. In the illustrated example of FIG. 9, control system 262 may vary the rate of extrusion, temperature, or magnetic field strength dynamically based on, for example, measurements (e.g., real-time) of the density and/or location of reflective elements 232, by monitoring system 264. Monitoring system 264 may be capable of sensing the location, either specifically or generally, of magnetic light reflective elements 232. For example, monitoring system 264 may include at least one sensing system for sensing the arrangement of magnetic light reflective elements 232 within the transparent, elongated body.

In some examples, the sensing system features a source, detector, and one or more focusing or filtering devices configured to work with radiation. The radiation may be light, ultrasound, x-rays, terahertz radiation, other known radiation, or any combination thereof. The presence and location of the magnetic light reflective elements 232 may be determined by the presence or absence of radiation in two or more measurements. For example, an optical testing method may involve shining a light into elongated body 210 perpendicular to the direction of extrusion, and monitoring the results with an image sensor. The pattern and intensity of the light hitting the sensor may vary based on how much the reflective elements redirect radiation. The sensor and/or light emitter may be rotated around elongated body 210, testing it from all angles. The light source may be, for example, a laser scanning across the diameter of the extrusions, or a collimated beam of light of the same width. Control system 262 may utilize the data collected from the image sensor to do at least one of the following: create a 3D model of the reflective array, compare the 3D model to an ideal arrangement, or compare raw data with saved data measured in the same manner from one or more ideal configurations produced previously. In another example, inductive sensing may be employed. One or more sensing coils, shielded from the field locating the reflective elements, may sense the depth of the particles within the material. Control system 262 may use the concentration of reflective elements to interpret raw data from the sensing coils into a measure of their location. Based on one or more magnetic light reflective elements 232 being out of position, control system 262 may adjust the electromagnetic field to alter the arrangement during application of the varying EM field, e.g., to apply more or less intense or differently directed electromagnetic field in a certain area of elongated body 210, or scrap/recycle a non-conforming section and apply corrections to make the next section conform. For example, control system 262 may dynamically change the electromagnets current and voltage values based on the amount and location of metal in their fields, e.g., to detect the uniformity of the distribution of the reflecting elements. Alternatively, between two or more stages of the groups of reflecting elements, arrays of smaller inductors could be located around elongated body 110 to detect the depth/concentration of the reflecting elements.

FIGS. 7 and 9 also show the transparent, elongated body 210 hardening to form light directing element 100. The hardening step may include any now known or later developed process for hardening the material of elongated body 110, which may depend on, among other things, the material, dimensions of the body, or material of magnetic reflective elements 232. The hardening step may include, for example, exposure over time, or exposure to certain temperatures, lighting, chemicals, etc.

In some examples, additive manufacturing (e.g., three-dimensional ("3D") printing) may be used to create light directing element 100. Ink or resin based 3D printing processes may be well suited to this application, because the reflective elements 132 may be aligned and/or deposited uniquely in each layer. Additionally, with a 3D printed device, reflective elements 132 may simply be one or more boundaries within the bulk material of elongated body 110.

Figure 10:
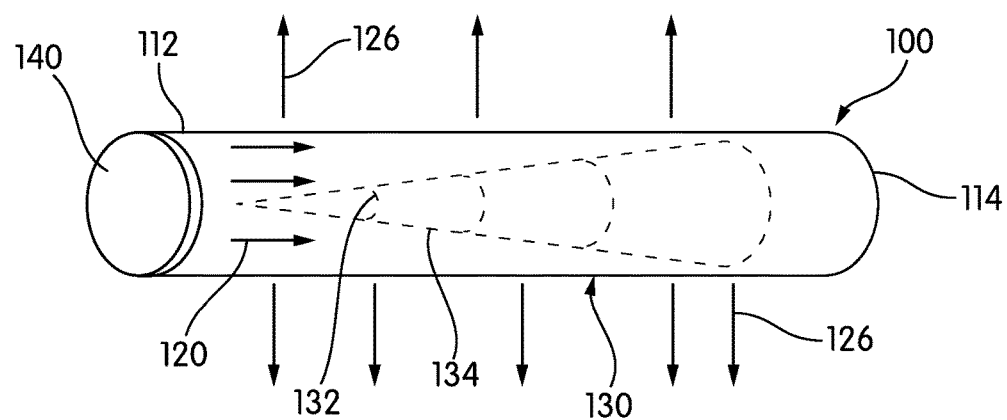
FIG. 10 shows a perspective view of a step of a method according to example systems, methods, and apparatuses of the disclosure.

FIG. 10 shows coupling a light emitter 140 to at least one end 112 (shown), 114 of elongated body 110 for emitting a light 120 axially into the transparent, elongated body to strike the at least one axially enlarging reflective array 134, and exiting as exiting light 126.

Figure 11:
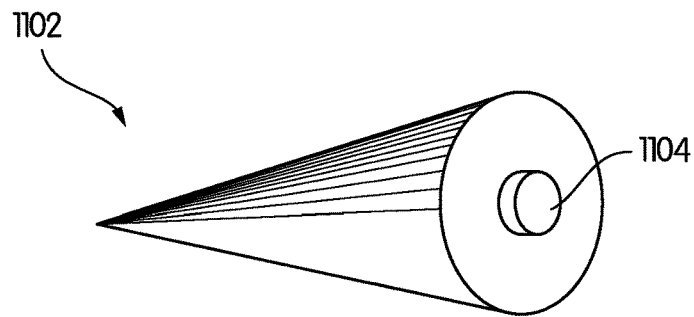
FIGS. 11-14 show various example diffusers according to example systems, methods, and apparatuses of the disclosure.
Figure 12:
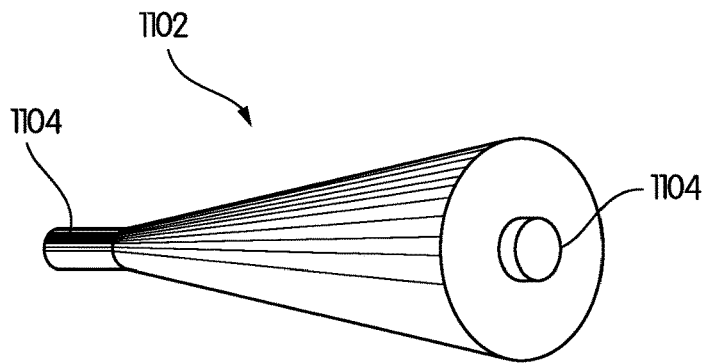
Figure 13:
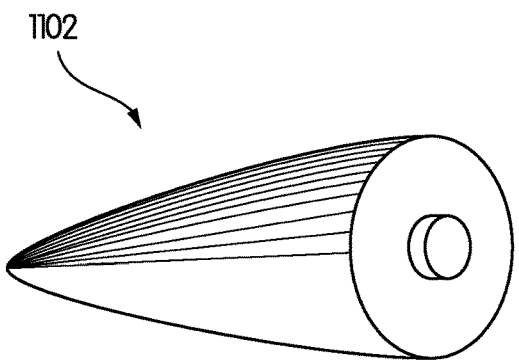
Figure 14:
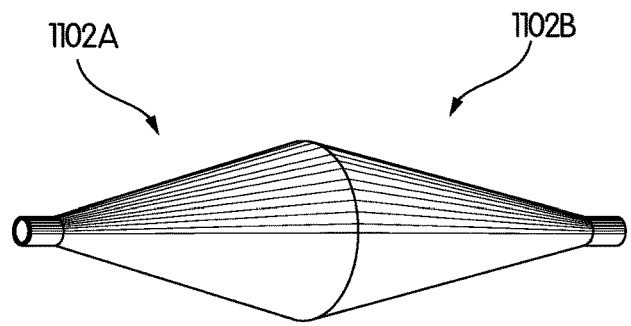

As mentioned above, the diffuser 130 may be a solid conical structure, such as the diffuser 1102 shown in FIG. 11. In some examples, the diffuser 1102 may comprise a first sprue or alignment pin 1104 disposed on one end of the diffuser 1102. In some examples, such as illustrated in FIG. 12, the diffuser 1102 may comprise a second sprue or alignment pin 1104 disposed on a second end of the diffuser 1102. In some examples, the second sprue or alignment pin 1104 may make the diffuser 130 have a truncated cone or frusto-conical structure. In some examples, the diffuser 1102 may have a curved exterior (e.g., parabolic, hyperbolic, exponential, etc.) such as illustrated in FIG. 13. The diffuser 1102 may be created by casting the diffuser 1102 into shape using a single reflective material, in some examples. In some examples, the diffuser 1102 may be created by injection molding reflective material into a desired shape. In some examples, the diffuser 1102 may be created with a first material, and subsequently a second material (e.g., a reflective coating) may be applied (e.g., casted, painted, wrapped) around the first material. In some examples, two diffusers 1102A, 1102B may be attached, created, molded, or cast together, as illustrated in FIG. 14. In the illustrated example of FIG. 14, light emitters may be applied at either end of the two diffusers 1102A, 1102B, thereby doubling the length of a corresponding light emitting element in which the two diffusers 1102A, 1102B may be disposed. The diffuser 1102 (1102A and 1102B) may comprise a single reflective material in some examples. However, in other examples, the diffuser 1102 may comprise a first material and a second material (e.g., a reflective coating) surrounding the first material.

Figure 15:
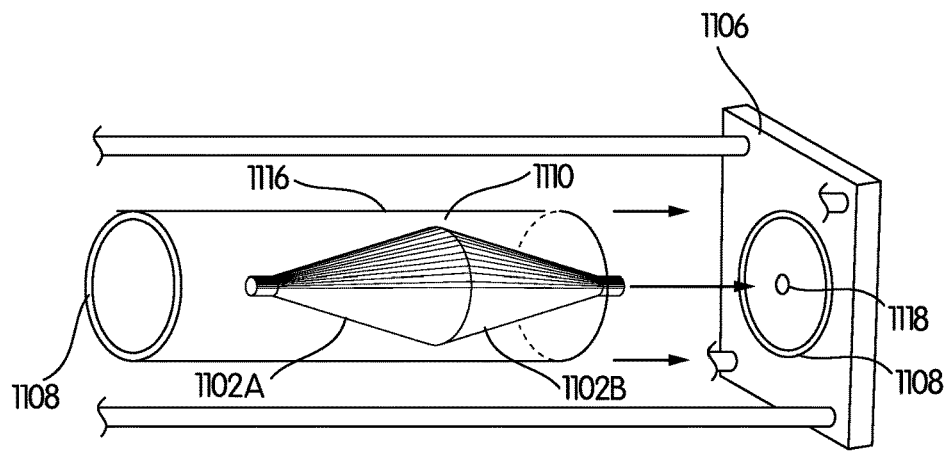
FIG. 15 shows a method of manufacture of example systems, methods, and apparatuses of the disclosure.

FIG. 15 illustrates an example method of manufacture for a light emitting element 1100 comprising the two diffusers 1102A, 1102B. One or more plates 1106 may be used to form an elongated body 1110 between a first O-ring 1108 on a first end 1112 and a second O-ring 1108 on a second end 1114. The elongated body 1110 may be formed by clamping a tube between the one or more plates 1106 and filling the tube with casting material. The tube may bond with the casting material and become the exterior surface 1116 of the elongated body 1110. The casting material and the exterior surface 1116 may be optically transparent resin, acrylic, plastic, glass, or any combinations thereof. The two diffusers 1102A, 1102B may be inserted within the exterior surface 1116 prior to filling the tube with casting material and may be held in place by slots 1118 within the one or more plates 1106. In some examples, the sprues or alignment pins 1104 may be inserted into the slots 1118 within the one or more plates 1106 to suspend the two diffusers 1102A and 1102B centrally within the exterior surface 1116 prior to casting. The first O-ring 1108 on the first end 1112 and the second O-ring 1108 on the second end 1114 may create a seal to prevent air leaks during a pressure casting or vacuum degassing operation. Once the casting material fills the tube, the casting material may be cured. The casting material may wet bond to the exterior surface 1116 to minimize internal reflections. In some examples, single diffuser 1102 light emitting elements may be cast in a similar fashion. Alternatively, the light emitting elements described herein may be 3D printed. In some examples, the casting material may bond to itself without leaving an optical boundary.

FIG. 16 illustrates a cross-sectional view of a beam collimator 1600 in the form of an example parabolic reflector, which may be used with one or more light emitters described herein. The beam collimator 1600 may be parabolic in shape and may be configured to reflect light from a light emitter disposed at a center 1602 of the beam collimator 1600. For example, one or more LEDs may be disposed at the center 1602 of the beam collimator 1600, which may reflect light in a collimated beam pattern. The beam collimator 1600 may be mounted into a mold assembly prior to casting, or attached to a formed elongated body. The beam collimator 1600 and/or light emitter may be cast in a transparent material with beneficial light transmission characteristics. In some examples, light may reach the surface of the light emitting element better when the beam collimator 1600 and/or light emitter are cast into the device, which may reduce reflections and/or scattering among the beam collimator 1600, light emitter, and surface of the elongated body.

Figure 17:
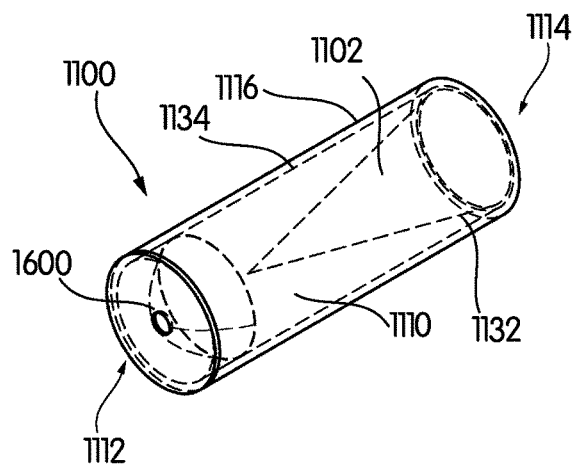
FIGS. 17-18 show a light emitting element with a beam collimator and a conical diffuser according to example systems, methods, and apparatuses of the disclosure.

FIG. 17 illustrates a light emitting element 1100 with a diffuser 1102 and a beam collimator 1600 disposed within an elongated body 1110. In some examples, the diffuser 1102 may be defined by a boundary 1132, which may separate the elongated body 1110 from the diffuser 1102. As described with reference to FIGS. 11-15, the diffuser 1102 may be a solid cone of reflective material. Alternatively, reflective material (e.g., a reflective coating) may be disposed between the diffuser 1102 and the elongated body 1110 along boundary 1132. In some examples, the reflective material may face (or partially face) towards exterior surface 1116. In some examples, the diffuser 1102 may be hollow. In some examples, light 1120 may be reflected and/or refracted along boundary 1132 based on the difference of materials between elongated body 1110 and diffuser 1102. In some examples, light 1120 from a first end 1112 may be reflected along boundary 1132 and light from a second end 1114 may be refracted along boundary 1132, such that a single diffuser 1102 may be used. In some examples, light 1120 from the first end 1112 may be reflected along a boundary 1132A and light from the second end 1114 may be reflected along a boundary 1132B, such that multiple diffusers 1102 may be used. Light 1120 may be reflected or refracted along boundary 1132 and may exit exterior surface 1116 as exiting light 1126 (FIG. 20).

Figure 18:
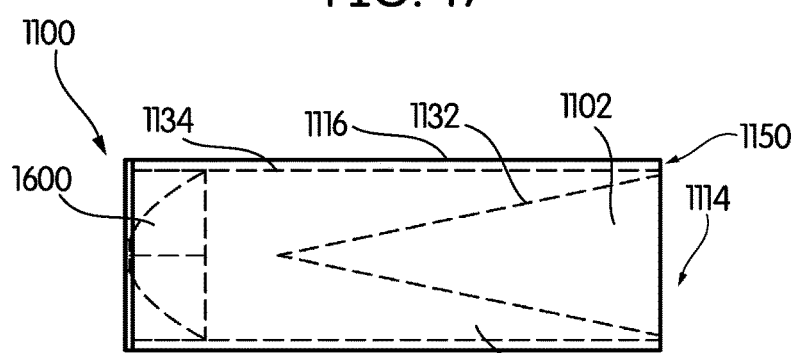

As illustrated in FIGS. 17-18, the largest end of the diffuser 1102 may terminate shy of the exterior surface 1116, identified by boundary 1134. A gap 1150 may be formed between boundary 1134 and exterior surface 1116, which may enable more uniform distribution of light. Additionally or alternatively, gap 1150 may comprise a light converting layer. In some examples, the largest end of the diffuser 1102 may terminate at exterior surface 1116, such that no gap exists.

Figure 19:
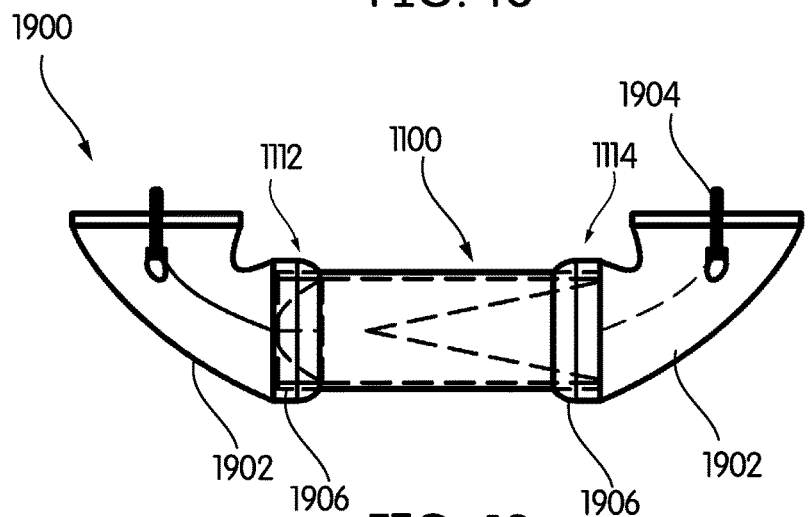
FIG. 19 shows an application of a light emitting element according to example systems, methods, and apparatuses of the disclosure.

FIG. 19 illustrates an example implementation of the light directing element 1100, e.g., as a handle 1900. The example light directing element 1100 may be surrounded by one or more end caps 1902, which may surround and support the light directing element 1100. The one or more end caps 1902 may attach to structure, such as, for example, a wall, via one or more fasteners 1904. One or more light emitters may be disposed in one or more of the end caps 1902 to direct light into the elongated body 1110 from the first end 1112 and/or the second end 1114. Portions 1906 of the end caps 1902 which surround and support the light directing element 1100 may also be transparent to enable disinfecting properties to such portions.

Figure 20:
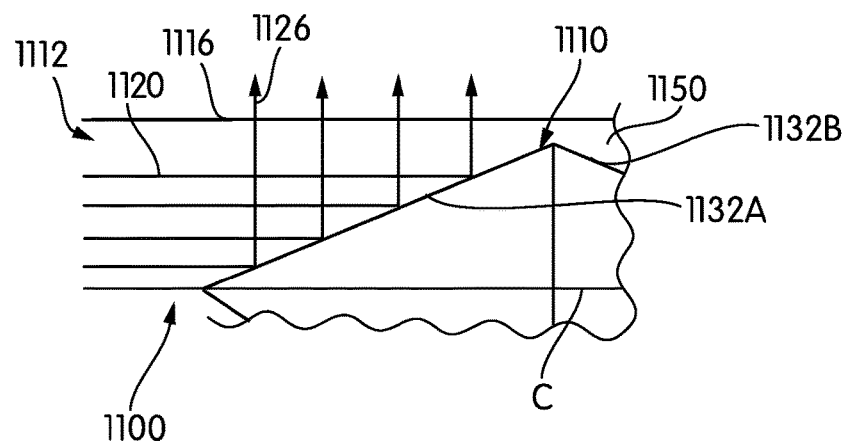
FIGS. 20-21 show light reflective/refractive patterns according to example systems, methods, and apparatuses of the disclosure.

As illustrated in FIG. 20, one or more rays of light 1120 may enter elongated body 1110 near centerline C of elongated body 1110 and may strike a portion of boundary 1132A of diffuser 1102 nearest a respective end 1112 and may be redirected toward exterior surface 1116. One or more rays of light 1120 slightly farther from centerline C may strike a second portion of boundary 1132, which may be positioned slightly farther into elongated body 110. The one or more rays of light 1120 that strike the second portion of boundary 1132A may be redirected toward exterior surface 1116. Because the boundary 1132A may be continuous, any number of rays of light 1120 may be reflected towards exterior surface 1116 and enable a uniform or near uniform illumination of exterior surface 1116. As illustrated in FIGS. 11-23, the boundary (e.g., boundary 1132A) may have a progressively decreasing distance from exterior surface 1116 as the distance from the light emitter increases. In some examples, the elongated body 1110 may comprise multiple boundaries 1132A, 1132B, wherein each boundary 1132A, 1132B may be any length of elongated body 110 as desired, e.g., a 50/50 split, a 30/70 split, etc. Boundary 1132B may perform similarly as boundary 1132A with light emitted from a second end 1114 opposite the first end 1112. Although FIG. 20 illustrates light 1120 above centerline C, light 1120 may similarly reflect below centerline C in a similar fashion.

Figure 21:
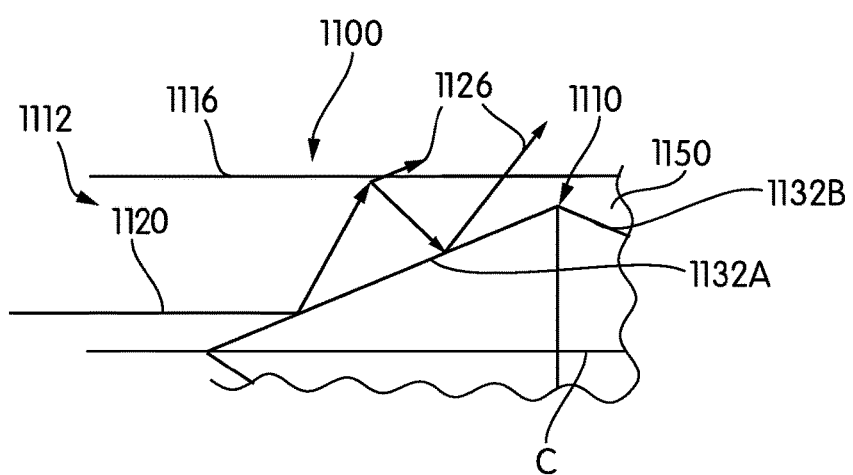

In some examples, like the example illustrated in FIG. 21, the light 1120 may not reflect directly out of exterior surface 1116. The path of light 1120 may depend on a number of factors including the angle of boundary 1132A, the materials of elongated body 1110 and/or boundary 1132A, etc. In some examples, the light 1120 may be reflected off of boundary 1132A towards exterior surface 1116 at angle different from ninety degrees. At such an angle, the light 1120 may be partially refracted externally and/or partially reflected internally at the exterior surface 1116. Any internally reflected light 1120 may be reflected again at boundary 1132A towards exterior surface 1116. In some examples, light 1120 may exit at exterior surface 1116, or may be refracted externally, and reflected internally again. Any light 1120 exiting exterior surface 1116 may create exiting light 1126. Such external refraction and/or internal reflection may further the uniform illumination of light emitting element 1100. The external refraction and/or internal reflection may be configured based on the materials used for elongated body 1110, boundary 1132A, and material outside elongated body 1110 (e.g., air, water, etc.), the angle of boundary 1132A, etc. While only one ray of light 1120 is illustrated in FIG. 21, any number of rays of light 1120 may be applied to boundary 1132A or 1132B and may reflect/refract as described herein.

Figure 22:
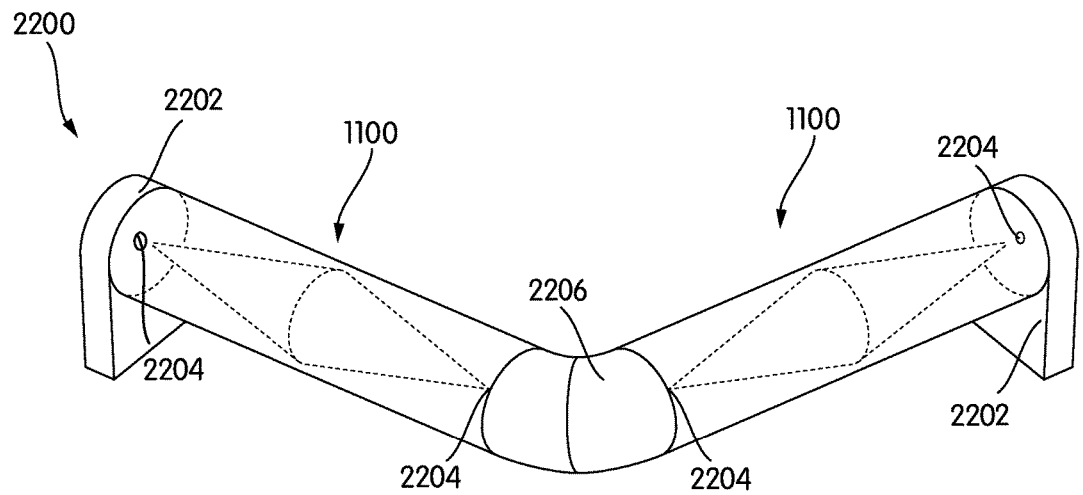
FIGS. 22-23 show examples of extended length applications of light emitting elements according to example systems, methods, and apparatuses of the disclosure.
Figure 23:
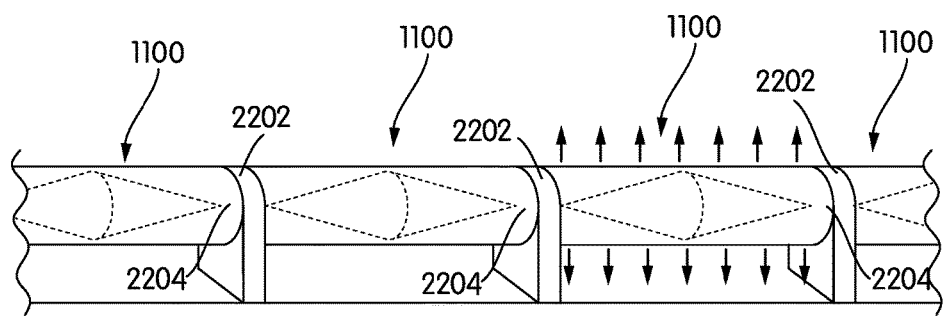

In some examples, the light directing element 1100 may be around one foot in length. In some examples, the light directing element 1100 may be any length such that light exiting exterior surface 1116 remains uniform or nearly uniform. In some examples, as illustrated in FIGS. 22-23, one or more light directing elements 1100 may be used together to enable an increased length light directing system 2200. In some examples, a plurality of end caps 2202 may be placed between two adjacent light directing elements 1100. In some examples, the end caps 2202 may comprise one or more light emitters 2204 on one or more sides of the end caps 2202 such that light may be directed into the two adjacent light directing elements 1110 by a single end cap 2202.

Similarly, as illustrated in FIG. 22, angled end caps 2206 may be used between two adjacent light directing elements 1100 at various angles. The angled end caps 2206 may be flexible or rigid and may be configured for any angle between two adjacent light directing elements 1100. The angled end caps 2206 may comprise one or more light emitters 2204 on one or more sides of the angled end caps 2206 such that light may be directed into the two adjacent light directing elements 1100 by a single angled end cap 2206. In such examples, any number of light directing elements 1100 may be connected together at various angles for applications such as, for example, non-linear objects (e.g., hand railing for stairs with landings or corners), extremely lengthy objects, etc. The end caps 2202 and the angled end caps 2206 may be minimally sized to be non-invasive and to reduce the amount of non-illuminated and/or non-disinfected surface area. Alternatively, fiber optics may be utilized to provide light emission in non-linear light directing elements.

In some examples, the exterior surface 1116 may change colors as described above. In some examples, the exterior surface 1116 may change colors to indicate a level of bacteria (e.g., white color indicating bacteria is or is being disinfected, red color indicating bacteria not being disinfected, etc.).

A number of advantages may be apparent from the present disclosure. Light emitting elements 100, 1100 may provide internally illuminated elements with a decreased number of light emitters, because the diffusers described herein may more uniformly distribute light from one or more light emitters at one or more ends of the light emitting elements 100, 1100. Further, because there may be no light emitters disposed centrally within the light emitting elements 100, 1100, the diameter of the light emitting elements 100, 1100 may be narrower than light emitting elements with centrally disposed light emitters. Additionally, the exterior surface 116, 1116 of the corresponding light emitting elements 100, 1100 may enable non-hazardous internal generated disinfecting light for surface disinfection.

Light directing elements 100, 1100 may provide controlled internal illumination in elongated bodies, which may be mass produced. Further, since the elements may be solid, they may be better sealed against the elements, more structurally supportive, etc. Further, the weight and/or aesthetics of elements 100, 1100 may be more pleasant when not illuminated. Light directing elements 100, 1100 may also provide improved packaging because the light emitter may not be centrally within the body (e.g., it may be located on the ends of the body), which may allow better cooling of the light emitters. Light directing elements 100, 1100 may also provide more uniform light distribution and/or more uniform disinfection when disinfecting light is employed.

The terminology used herein is for the purpose of describing particular examples only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. "Approximately" as applied to a particular value of a range applies to both values, and unless otherwise dependent on the precision of the instrument measuring the value, may indicate at or around +/−10% of the stated value(s).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure.

An example light directing element may comprise an elongated body having a first end, a second end and an exterior surface, the elongated body being transparent or translucent to permit transmission of light axially and radially therethrough, a light emitter disposed at the first end of the elongated body, and a diffuser including at least one reflective element disposed within the elongated body, wherein the diffuser is configured to redirect light emitted from the light emitter uniformly towards the exterior surface and wherein the diffuser expands in cross-section towards the second end.

In some examples, the light directing element further comprises a second light emitter disposed at a second end of the elongated body and a second diffuser configured to redirect light emitted from the second light emitter uniformly towards the exterior surface, wherein the second diffuser expands in cross-section towards the first end.

In some examples, the diffuser and the second diffuser meet centrally between the first end and the second end.

In some examples, the diffuser comprises a conical shape that terminates a length from the exterior surface.

In some examples, the diffuser is configured to redirect the light toward the exterior surface with a substantially uniform irradiance at least 0.02 milliWatts per square centimeter (0.02 mW/cm$^2$) across the surface area of the exterior surface.

In some examples, the light emitter includes one or more of electroluminescent light emitters, light emitting diodes (LEDs), or lasers.

In some examples, at least a portion of the light emitted from the light emitter comprises disinfecting light with a wavelength in a range of 380 to 420 nanometers.

In some examples, the light directing element further comprises a beam collimator surrounding the light emitter and disposed within the elongated body.

In some examples, the light directing element further comprises at least one end cap, wherein the at least one end cap comprises the light emitter disposed at the first end of the elongated body.

An example light directing element may comprise a transparent or translucent body having a first end, a second end and an exterior surface, and a diffuser disposed within the transparent or translucent body and expanding in cross-section towards the second end, wherein the diffuser comprises at least one reflective element configured to redirect light axially transmitted from the first end radially towards the exterior surface.

In some examples, the light directing element further comprises a second diffuser configured to redirect light axially transmitted from the second end radially towards the exterior surface, wherein the second diffuser expands in cross-section towards the first end.

In some examples, the diffuser and the second diffuser meet centrally between the first end and the second end.

In some examples, the diffuser comprises a conical shape that terminates a length from the exterior surface.

In some examples, the diffuser comprises an axially enlarging array of reflective elements.

In some examples, the diffuser is configured to redirect the light toward the exterior surface with a substantially uniform irradiance at least 0.02 milliWatts per square centimeter (0.02 mW/cm$^2$) across an area of the exterior surface.

In some examples, at least a portion of the light comprises disinfecting light with a wavelength in a range of 380 to 420 nanometers.

In some examples, the light directing element further comprises a light emitter comprising one or more of electroluminescent light emitters, light emitting diodes (LEDs), or lasers.

In some examples, the light directing element further comprises a beam collimator surrounding the light emitter and disposed within the elongated body.

An example method comprises casting a conically shaped diffuser comprising at least one alignment pin, inserting the at least one alignment pin into a first plate, inserting a tube into the first plate surrounding the conically shaped reflective diffuser, and filling the tube with casting material.

In some examples, the method further comprises casting a second conically shaped diffuser comprising at least one second alignment pin, inserting the at least one second alignment pin into a second plate, and clamping the tube between the first plate and the second plate.

In some examples, the method further comprises coating the conically shaped diffuser with reflective material.

An example light directing element may comprise an elongated body having a first end, a second, opposing end and an exterior surface, the elongated body being transparent or translucent to permit transmission of light axially therethrough from one end to the other end, and a diffuser including a plurality of light reflective elements arranged within the elongated body to collectively create at least one axially, enlarging reflective array to progressively redirect light toward the exterior surface as the light passes axially through the elongated body.

In some examples, the at least one axially enlarging reflective array includes a first axially enlarging reflective array facing the first end of the elongated body for redirecting light entering the first end, and a second axially enlarging reflective array facing the second, opposing end of the elongated body for redirecting light entering the second, opposing end.

In some examples, each axially enlarging reflective array has a progressively decreasing distance from the exterior surface as the array extends from an end thereof axially into the elongated body.

In some examples, each axially enlarging reflective array includes groups of light reflective elements collectively forming a series of increasing radius arcs.

In some examples, each group of light reflective elements collectively forming the series of increasing diameter arcs are circles, creating a conical configuration.

In some examples, the plurality of light reflective elements are arranged within the elongated body to redirect the light toward the exterior surface with a substantially uniform irradiance across a surface area of the exterior surface.

In some examples, the light has an irradiance of no less than 0.02 milliWatts per square centimeter (0.02 mW/cm2) across the surface area of the exterior surface.

In some examples, the light directing element may further comprise a light emitter operably coupled to at least one end of the elongated body for emitting a light axially into the elongated body to strike the at least one axially enlarging reflective array.

In some examples, the at least one axially enlarging reflective array includes a pair of axially enlarging reflective arrays, one array having a respective smaller end facing the first end of the elongated body and the other array having a respective smaller end facing the second, opposing end of the elongated body, and wherein the light emitter includes a light emitter operably coupled to one end of the elongated body for emitting the light axially into the elongated body to strike each of the pair of axially enlarging reflective arrays.

In some examples, the light emitter includes one or more of electroluminescent light emitters, light emitting diodes (LEDs), or lasers.

In some examples, the light has at least a portion thereof having a wavelength in a range of 380 to 420 nanometers, creating a disinfecting light.

In some examples, the disinfecting light is white.

In some examples, the elongated body is a solid cylinder.

In some examples, each light reflecting element includes a planar, magnetic body.

In some examples, each light reflecting element has a surface area of less than approximately 4 square millimeters.

In some examples, each light reflective element has a magnetic field therein configured to position the light reflective element in a location to direct light to the exterior surface upon exposure to a controlled electromagnetic field.

An example method comprises extruding a transparent, elongated body having a plurality of magnetic light reflective elements within the body, the transparent, elongated body including a first end, a second, end and an exterior surface, prior to hardening of the transparent, elongated body, creating a diffuser by applying a varying electromagnetic (EM) field along at least a portion of the transparent, elongated body to arrange the plurality of magnetic light reflective elements within the elongated body to collectively create at least one axially, enlarging reflective array to progressively redirect light toward the exterior surface as light passes axially through the elongated body, and hardening the transparent, elongated body.

In some examples, the method further comprises monitoring the arrangement of the plurality of magnetic light reflective elements within the transparent, elongated body during the applying the varying EM field, and in response to one or more magnetic light reflective elements being out of position, adjusting the electromagnetic field to change the arrangement during the applying the varying EM field.

In some examples, the monitoring includes at least one of optically, ultrasonically, inductively or electromagnetically sensing the arrangement of the plurality of magnetic light reflective elements within the transparent, elongated body.

In some examples, the applying the varying EM field arranges the plurality of magnetic light reflective elements to have a progressively decreasing distance from the exterior surface as the array extends from an end thereof axially into the transparent, elongated body.

In some examples, each axially enlarging reflective array includes groups of magnetic light reflective elements collectively forming a series of increasing radius arcs.

In some examples, each group of magnetic light reflective elements collectively forming the series of increasing diameter arcs are circles, creating a conical configuration.

In some examples, the at least one axially enlarging reflective array includes a first axially enlarging reflective array facing the first end of the transparent, elongated body for redirecting light entering the first end, and a second axially, enlarging reflective array facing the second end of the transparent, elongated body for redirecting light entering the second end.

In some examples, each magnetic light reflecting element includes a planar body.

In some examples, the applying the varying EM field arranges the plurality of magnetic light reflective elements in groups in a series of increasing diameter circles from the first end towards the second end.

In some examples, the applying the varying EM field arranges the plurality of magnetic light reflective elements in groups in at least a portion of a cone configuration.

In some examples, the applying the varying EM field arranges the plurality of magnetic light reflective elements within the transparent, elongated body to redirect light entering the elongated body toward the exterior surface with a substantially uniform irradiance across a surface area of the exterior surface.

In some examples, the method further comprises coupling a light emitter to at least one end of the elongated body for emitting a light axially into the transparent, elongated body to strike the at least one axially enlarging reflective array.

In some examples, the light has at least a portion thereof having a wavelength in a range of 380 to 420 nanometers, creating a disinfecting light.

In some examples, the disinfecting light is white.

In some examples, each magnetic light reflecting element includes a planar body.

In some examples, the applying the varying EM field includes applying the varying EM field around the at least a portion of the transparent, elongated body.

An example system may comprise a first light emitting element comprising a first diffuser, wherein the first diffuser expands in cross-section towards a first end of the first light emitting element and wherein the first diffuser comprises at least one reflective element configured to redirect light axially transmitted from a second end of the first light emitting element radially towards an exterior surface of the first light emitting element, a second light emitting element comprising a second diffuser, wherein the second diffuser expands in cross-section towards a first end of the second light emitting element and wherein the second diffuser comprises at least one reflective element configured to redirect light axially transmitted from a second end of the second light emitting element radially towards an exterior surface of the second light emitting element, and an end cap disposed between the first light emitting element and the second light emitting element.

What is claimed is:

1. A light directing element comprising:
    an elongated body having a first end, a second end and an exterior surface, the elongated body being transparent or translucent to permit transmission of light axially and radially therethrough;
    a light emitter disposed at the first end of the elongated body;
    a diffuser including at least one reflective element disposed within the elongated body, wherein the diffuser is configured to redirect axially emitted light from the light emitter radially towards the exterior surface and wherein the diffuser expands in cross-section towards the second end;
    a first end cap disposed at, and configured to surround, the first end of the elongated body; and
    a second end cap disposed at, and configured to surround, the second end of the elongated body;
    wherein the first end cap and the second end cap support the elongated body a distance from an adjacent structure.

2. The light directing element of claim 1, further comprises:
    a second light emitter disposed at the second end of the elongated body; and
    a second diffuser configured to redirect axially emitted light from the second light emitter radially towards the exterior surface, wherein the second diffuser expands in cross-section towards the first end.

3. The light directing element of claim 1, wherein the diffuser comprises a conical shape that terminates a distance from the exterior surface.

4. The light directing element of claim 1, wherein at least a portion of the light emitted from the light emitter comprises disinfecting light with a wavelength in a range of 380 to 420 nanometers and wherein the diffuser is configured to redirect the portion of the light toward the exterior surface with a substantially uniform irradiance at least 0.02 milliWatts per square centimeter (0.02 mW/cm$^2$) across an entire area of the exterior surface.

5. The light directing element of claim 1, further comprising a beam collimator surrounding the light emitter and disposed within the elongated body.

6. The light directing element of claim 2, wherein the diffuser and the second diffuser contact centrally between the first end and the second end.

7. A light directing element comprising:
    a transparent or translucent body having a first end, a second end and an exterior surface; and
    a diffuser disposed within the transparent or translucent body and expanding in cross-section towards the second end, wherein:
        the diffuser comprises at least one reflective element configured to redirect light axially transmitted from the first end radially towards the exterior surface;
        at least a portion of the light comprises disinfecting light with a wavelength in a range of 380 to 420 nanometers; and
        the diffuser is configured to redirect the at least the portion of the light toward the exterior surface with a substantially uniform irradiance at least 0.02 milliWatts per square centimeter (mW/cm$^2$) across an area of the exterior surface.

8. The light directing element of claim 7, further comprising:
    a second diffuser configured to redirect light axially transmitted from the second end radially towards the exterior surface, wherein the second diffuser expands in cross-section towards the first end.

9. The light directing element of claim 7, wherein the diffuser comprises a conical shape that terminates a distance from the exterior surface.

10. The light directing element of claim 7, wherein the diffuser comprises an axially enlarging array of reflective elements.

11. The light directing element of claim 7, further comprising a light emitter comprising one or more of electroluminescent light emitters, light emitting diodes (LEDs), or lasers.

12. The light directing element of claim 8, wherein the diffuser and the second diffuser contact centrally between the first end and the second end.

13. The light directing element of claim 11, further comprising a beam collimator surrounding the light emitter and disposed within the transparent or translucent body.

14. A method comprising:
    creating a conically shaped diffuser comprising at least one alignment pin;
    inserting the at least one alignment pin into a first plate;
    inserting a tube into the first plate and surrounding the conically shaped diffuser; and
    filling the tube with material.

15. The method of claim 14, further comprising:
    creating a second conically shaped diffuser comprising at least one second alignment pin;
    inserting the at least one second alignment pin into a second plate; and
    clamping the tube between the first plate and the second plate.

16. The method of claim 14, further comprising:
    coating the conically shaped diffuser with reflective material.

17. A system comprising:
    a first light emitting element comprising a first diffuser, wherein the first diffuser expands in cross-section towards a first end of the first light emitting element and wherein the first diffuser comprises at least one reflective element configured to redirect light axially transmitted from a second end of the first light emitting element radially towards an exterior surface of the first light emitting element;

a second light emitting element comprising a second diffuser, wherein the second diffuser expands in cross-section towards a first end of the second light emitting element and wherein the second diffuser comprises at least one reflective element configured to redirect light axially transmitted from a second end of the second light emitting element radially towards an exterior surface of the second light emitting element; and an end cap disposed between the first light emitting element and the second light emitting element.

\* \* \* \* \*

UNITED STATES PATENT AND TRADEMARK OFFICE
CERTIFICATE OF CORRECTION

PATENT NO. : 10,309,614 B1  
APPLICATION NO. : 16/022440  
DATED : June 4, 2019  
INVENTOR(S) : Nicholas Jones et al.

Page 1 of 1

It is certified that error appears in the above-identified patent and that said Letters Patent is hereby corrected as shown below:

On the Title Page

Item (73) should read: (73) Assignee: Vital Vio, Inc., Troy, NY (US)

Signed and Sealed this  
Thirty-first Day of December, 2019

Andrei Iancu  
*Director of the United States Patent and Trademark Office*